United States Patent
Ma et al.

(10) Patent No.: US 9,487,831 B2
(45) Date of Patent: Nov. 8, 2016

(54) USE OF ANNEXIN A3 AS A DIAGNOSTIC AND PROGNOSTIC BIOMARKER AND THERAPEUTIC TARGET FOR TREATING HEPATOCELLULAR CARCINOMA

(71) Applicant: The University of Hong Kong, Hong Kong (CN)

(72) Inventors: Stephanie Kwai Yee Ma, Hong Kong (CN); Man Tong, Hong Kong (CN); Xin-Yuan Guan, Hong Kong (CN)

(73) Assignee: VERSITECH LIMITED, Hong Kong (CN)

( * ) Notice: Subject to any disclaimer, the term of this patent is extended or adjusted under 35 U.S.C. 154(b) by 0 days.

(21) Appl. No.: 14/485,206

(22) Filed: Sep. 12, 2014

(65) Prior Publication Data

US 2015/0071933 A1    Mar. 12, 2015

Related U.S. Application Data

(60) Provisional application No. 61/877,061, filed on Sep. 12, 2013.

(51) Int. Cl.

| | |
|---|---|
| *G01N 33/574* | (2006.01) |
| *C12Q 1/68* | (2006.01) |
| *C12N 15/113* | (2010.01) |
| *G01N 33/50* | (2006.01) |
| *C07K 16/18* | (2006.01) |

(52) U.S. Cl.
CPC ............. *C12Q 1/6886* (2013.01); *C07K 16/18* (2013.01); *C12N 15/1137* (2013.01); *G01N 33/5011* (2013.01); *G01N 33/57438* (2013.01); *C07K 2317/73* (2013.01); *C07K 2317/76* (2013.01); *C12N 2310/11* (2013.01); *C12Q 2600/118* (2013.01); *C12Q 2600/158* (2013.01); *C12Y 301/04003* (2013.01); *G01N 2333/4718* (2013.01); *G01N 2333/916* (2013.01)

(58) Field of Classification Search
None
See application file for complete search history.

(56) References Cited

FOREIGN PATENT DOCUMENTS

CN    103116028    *    5/2013

OTHER PUBLICATIONS

Harashima et al J. Biochem. vol. 143 p. 537 (2008).*
Jia et al Proteome Science vol. 10:39, 9 pages, Jan. 2012.*
Tsai et al Proteome Science vol. 10:69, 14 pages (Mar. 2012).*
Translation of CN 103116028 (May 2013), 11 pages.*

* cited by examiner

*Primary Examiner* — Sheela J Huff
(74) *Attorney, Agent, or Firm* — Saliwanchik, Lloyd & Eisenschenk

(57) ABSTRACT

Annexin A3 (ANAX3) is utilized as a biomarker for the diagnosis and prognosis of hepatocellular carcinoma (HCC) and the utilization of a monoclonal antibody against ANXA3 or antisense polynucleotide against ANXA3 mRNA for the suppression or treatment of HCC, alone or in combination with other HCC treatment. Monoclonal antibody against ANXA3 can be administered for the suppression of tumor growth, metastasis, and chemoresistance.

6 Claims, 9 Drawing Sheets

Figure 1:
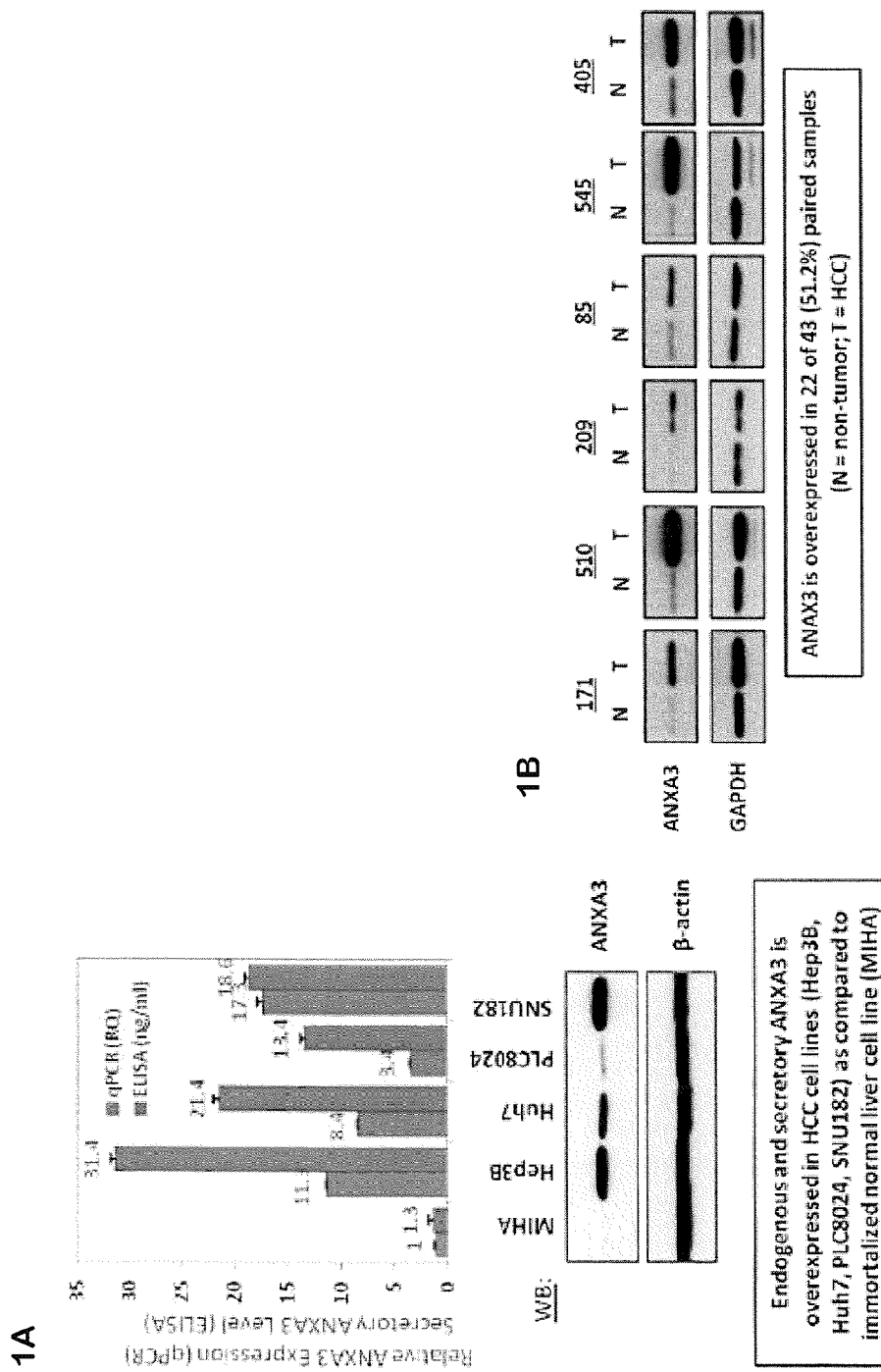
Figure 1:
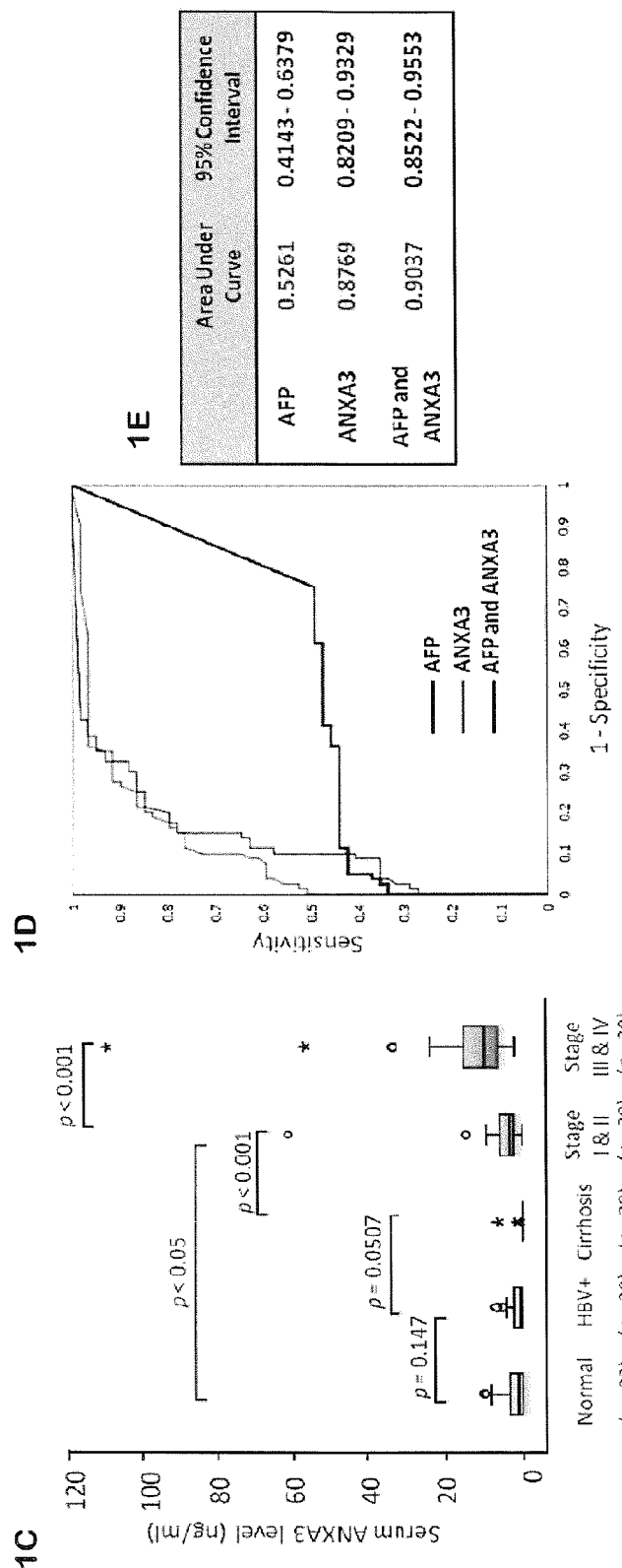

USE OF ANNEXIN A3 AS A DIAGNOSTIC AND PROGNOSTIC BIOMARKER AND THERAPEUTIC TARGET FOR TREATING HEPATOCELLULAR CARCINOMA

CROSS-REFERENCE TO RELATED APPLICATION

This application claims the benefit of U.S. Provisional Application Ser. No. 61/877,061, filed Sep. 12, 2013, which is hereby incorporated by reference in its entirety.

FIELD OF THE INVENTION

The present invention provides annexin A3 (ANAX3) as a biomarker for prediction and diagnosis of hepatocellular carcinoma (HCC) as well as a therapeutic target for HCC treatment. The current invention also provides a monoclonal antibody capable of binding to ANXA3 protein and a short hairpin ribonucleic acid (shRNA) capable of inhibiting ANXA3 protein expression as agents for HCC treatment.

BACKGROUND

Hepatocellular carcinoma (HCC) is the sixth most common cancer worldwide and is one of the most prevalent malignancies in Asia and locally in Hong Kong. Currently, the front-line treatment regimen for HCC includes hepatic resection and liver transplantation. However, these two potentially curative treatment options are limited by several factors, for example, (i) advanced stage at which the disease is usually diagnosed, (ii) underlying cirrhosis and poor hepatic reserve commonly associated with these patients, and (iii) shortage of available liver grafts.

It has been estimated that only 25% of the patients with HCC are eligible for potential curative treatments at the time of presentation. Several local ablation treatment protocols, such as percutaneous ethanol injection (PEI) or radiofrequency ablation (RFA), are also commonly practiced in cases of limited disease; but these methods are mainly for palliation and are applicable only to patients who meet stringent criteria with tumors localized to liver.

Chemotherapy either via transarterial chemoembolization (TACE) or systemic treatment is also available and is also administered as a pre-/post-surgical adjuvant therapy, yet the overall response rate to this treatment is low due to the highly chemotherapy resistant nature of HCC. Thus, there is an urgent need to elucidate the key genes in relation to recurrence and chemo-resistance in HCC, to develop better diagnostic and prognostic biomarkers for detection of HCC at an earlier stage, and to develop novel therapeutic approaches to more effectively treat the disease.

As molecular indicators of biological status, biomarkers detectable in blood can be useful for the clinical management of various disease states. Threshold concentrations can be utilized to identify the presence of various diseases. Common cancer biomarkers include prostate specific antigen (PSA) for prostate cancer and cancer antigen 125 (CA125) for ovarian cancer. Currently, serum α-fetoprotein (AFP) has been widely used for HCC diagnosis (MacDonald and Kelly, 1978). However, the serum AFP cut-off for detecting HCC in patients with co-existing liver diseases has not reached consensus with values ranging from 10 to 500 ng/ml (Taketa 1990, Johnson 2001, Gebo et al., 2002). The serum AFP test when used with the conventional higher cut-off point of 500 ng/ml revealed a sensitivity of about 50% and a specificity of more than 90% in detecting the presence of HCC in patients with co-existing liver disease (Johnson 2001). When used with lower cut-off values between 10 and 19 ng/ml, the sensitivity of the serum AFP test was 45% to 100% and with a specificity of 70% to 95% (Gebo et al., 2002).

Other common biomarkers for HCC include glypican-3 and des-gamma-carboxy prothrombin (DCP), but their uses are also limited in their sensitivity and specificity.

Therefore, the identification of a novel biomarker with better sensitivity and specificity is urgently required for a better diagnosis and prognosis of HCC.

With the advent of hybridoma technology for the production of humanized and murine-human chimeric monoclonal antibody, targeted cancer therapy can be achieved by the use of monoclonal antibodies (Adams and Weiner 2005). Monoclonal antibody therapy is proven to be effective in cancer treatment, for example, the use of anti-CD20 monoclonal antibody (Rituximab) for B-cell lymphoma (von Schilling 2003), anti-Her2 neutralizing monoclonal antibody (Herceptin) for metastatic breast cancer (Shak 1999, Willems et al., 2005) and anti-EGFR and anti-VEGF for metastatic colorectal cancer (Vanhoefer et al., 2004, Fernando and Hurwitz 2004). In fact, many monoclonal antibodies are currently undergoing clinical trials; thus further suggesting the usefulness of monoclonal antibodies for therapeutic purposes. Current molecular targets for the treatment of HCC are restricted to several cell signaling pathways, like EGFR, IGF-R1, PI3K/AKT/mTOR, RAS/RAF/MAPK, VEGF, etc., and although with some success, molecular targeted therapies (including monoclonal antibodies and small molecule inhibitors) for other pathways would be beneficial in HCC treatment.

ANXA3 belongs to the annexin family of $Ca^{2+}$-dependent phospholipid-binding proteins (Wu et al., 2013). Up-regulation of ANXA3 expression was recently detected in various tumor types including prostate, ovarian, lung, and breast cancers (Wozny et al., 2007, Kollermann et al., 2008, Schostak et al., 2009, Thoenes et al., 2010, Yan et al., 2007, Yan et al., 2010, Liu et al., 2009; Zeng et al., 2013). Serum ANXA3 levels were also found to be significantly up-regulated in ovarian cancer patients compared with healthy individuals (Yin et al., 2012). Furthermore, overexpression of ANXA3 was found to contribute to platinum resistance in ovarian cancer (Yan et al., 2007, Yan et al., 2010). Two recent studies have also found ANXA3 to be preferentially expressed in the $CD133^{+}$ liver cancer stem cell subset (Tsai et al., Proteome Sci 2012) and that ANXA3 is associated with multi-drug resistance (MDR) in 5-fluorouracil-resistant HCC cells BEL7402 (Tong et al., J Cell Biochem 2012). Yet, to date, no studies have addressed the clinical significance of endogenous and secretory ANXA3 in HCC, the role of ANXA3 in driving hepato-carcinogenesis, or the use of anti-ANAX3 antibody as a therapeutic regimen against HCC.

BRIEF SUMMARY

The present invention provides the use of ANAX3 as a biomarker for prediction, diagnosis, and prognosis of HCC and a therapeutic target for HCC treatment. The current invention also provides agents for treatment of HCC, for example, a monoclonal antibody capable of binding to ANXA3 protein, and short hairpin ribonucleic acid (shRNA) capable of inhibiting ANXA3 protein expression. These agents can be administered to the patients in need of HCC treatment either alone or in combination with other HCC treatments, for example, chemotherapy or radiotherapy.

In one embodiment, the present invention provides a method for predicting whether a subject is suffering from HCC, the method comprising:

(a) obtaining a biological sample from the subject, (b) detecting in the sample a level of expression for ANXA3 protein or mRNA, (c) comparing the expression level in (b) to a level of expression for ANXA3 in a control sample, and (d) diagnosing the presence of HCC in the subject if ANXA3 is overexpressed in the biological sample from the subject with respect to the control sample or diagnosing the absence of HCC in the subject if ANXA3 is expressed at a similar or lower level in the biological sample from the subject with respect to the control sample.

In another embodiment, the present invention provides a method for assessing prognosis of HCC in a subject is being treated for HCC, the method comprising:

(a) obtaining a biological sample from the subject, (b) detecting in the sample a level of expression for ANXA3 protein or mRNA, (c) comparing the expression level in (b) to a level of expression for ANXA3 in a control sample, and (d) assessing the prognosis of HCC in the subject as poor if ANXA3 is overexpressed in the biological sample from the subject with respect to the control sample or assessing the prognosis of HCC in the subject as good if ANXA3 is expressed at a similar or lower level in the biological sample from the subject with respect to the control sample.

In another aspect, the present invention provides a method for inhibiting HCC progression and/or treating HCC. In one embodiment, the method comprises administering to a subject in need of such treatment an effective amount of an ANXA3 inhibitor.

ANXA3 inhibitors useful according to the present invention include, but are not limited to, agents that inhibit ANXA3 protein activity, for example, antibodies against ANXA3 protein; and agents that reduce or inhibit the expression of ANXA3, for example, agents that inhibit the transcription, translation, or processing of ANXA3, for example, shRNAs against ANXA3 mRNA.

BRIEF DESCRIPTION OF THE SEQUENCES

SEQ ID NO: 1 is a portion of ANXA3 protein to which binds the monoclonal antibody against ANXA3 protein.

SEQ ID NO: 2 is a cDNA sequence corresponding to a portion of ANXA3 mRNA to which binds a specific shRNA against ANXA3 mRNA.

SEQ ID NO: 3 is another cDNA sequence corresponding to a portion of ANXA3 mRNA to which binds a specific shRNA against ANXA3 mRNA.

SEQ ID NO: 4 is the amino acid sequence of a human ANXA3 protein.

SEQ ID NO: 5 is a cDNA sequence corresponding to the nucleotide sequence of a human ANXA3 mRNA.

SEQ ID NO: 6 is a nucleotide primer sequence specific for ANXA3.

SEQ ID NO: 7 is a nucleotide primer sequence specific for ANXA3.

BRIEF DESCRIPTIONS OF THE DRAWINGS

FIG. 1A shows the endogenous and secretory ANXA3 expression in HCC cell lines (Hep3B, Huh7, PLC8024 and SNU182) as compared to the normal immortalized liver cell line, MIHA, as detected by qPCR, Western blot and ELISA assays. FIG. 1B shows a representative Western blot of increased ANXA3 protein expression in 6 pairs of matched primary HCC compared with non-tumor counterparts (Patients 171, 510, 209, 85, 545 and 405). FIG. 1C shows serum ANXA3 levels detected by quantitative ELISA in samples collected from normal healthy individuals (n=32), HBV carriers (n=20), patients with liver cirrhosis (n=20), patients with early stage HCC (Stage I and II) (n=30), and patients with advanced stage HCC (Stage III and IV) (n=30). FIG. 1D shows a graph of ROC analysis of sensitivity and specificity of AFP alone, ANXA3 alone and AFP/ANXA3 combination for HCC diagnosis in the same set of HCC patient samples. FIG. 1E shows a summary of the area under the curve for FIG. 1D and the corresponding 95% confidence interval.

Figure 2:
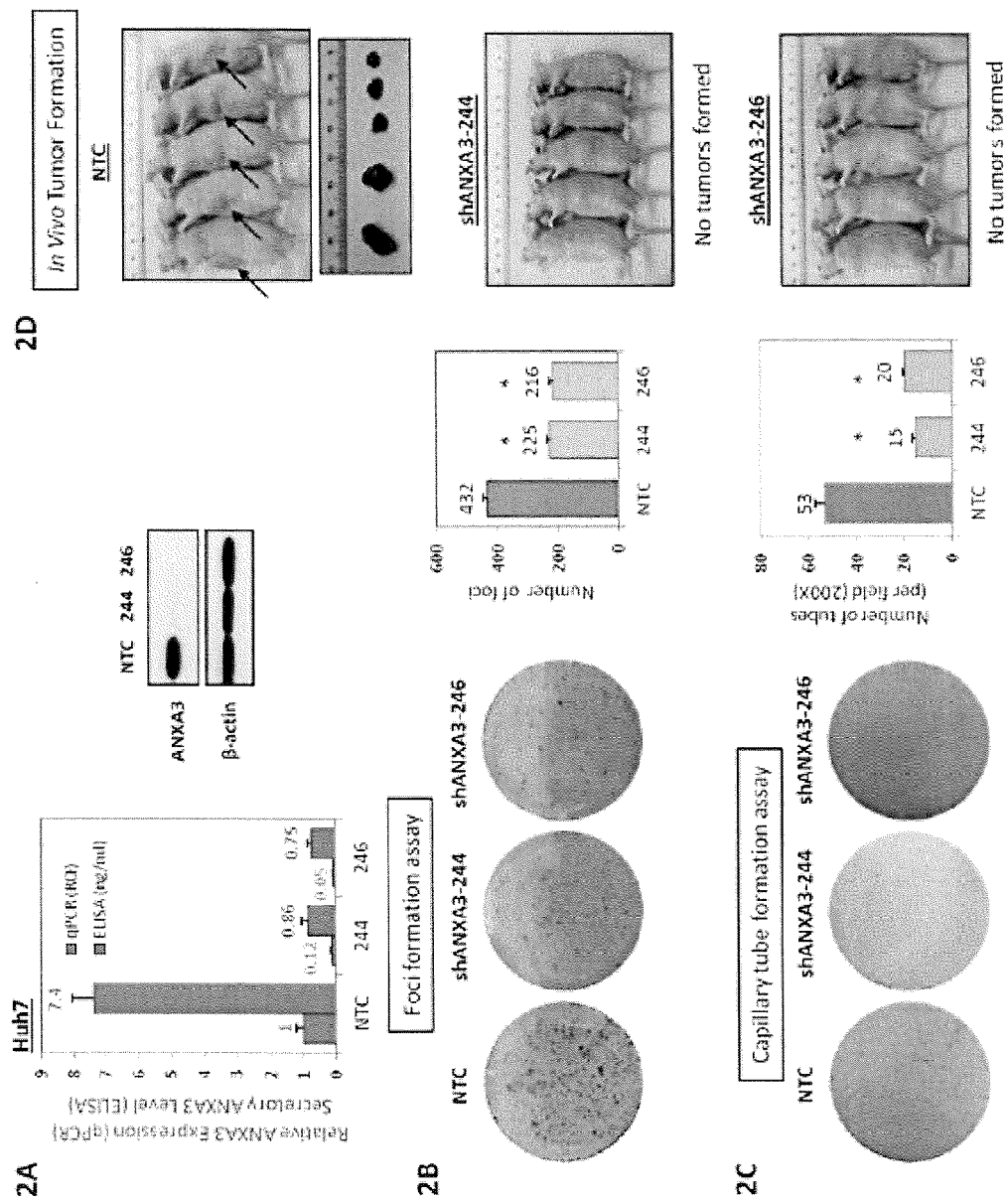
Figure 2:
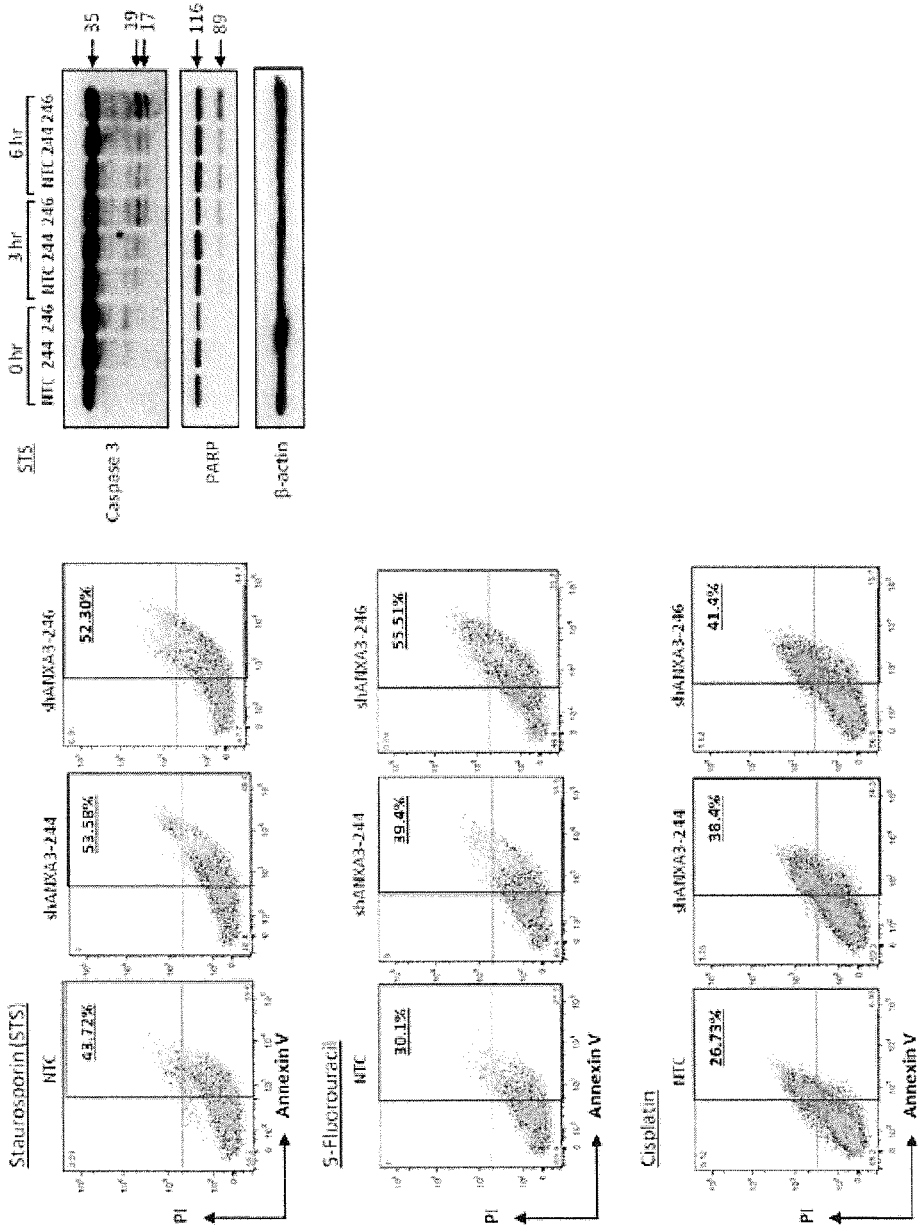
Figure 2:
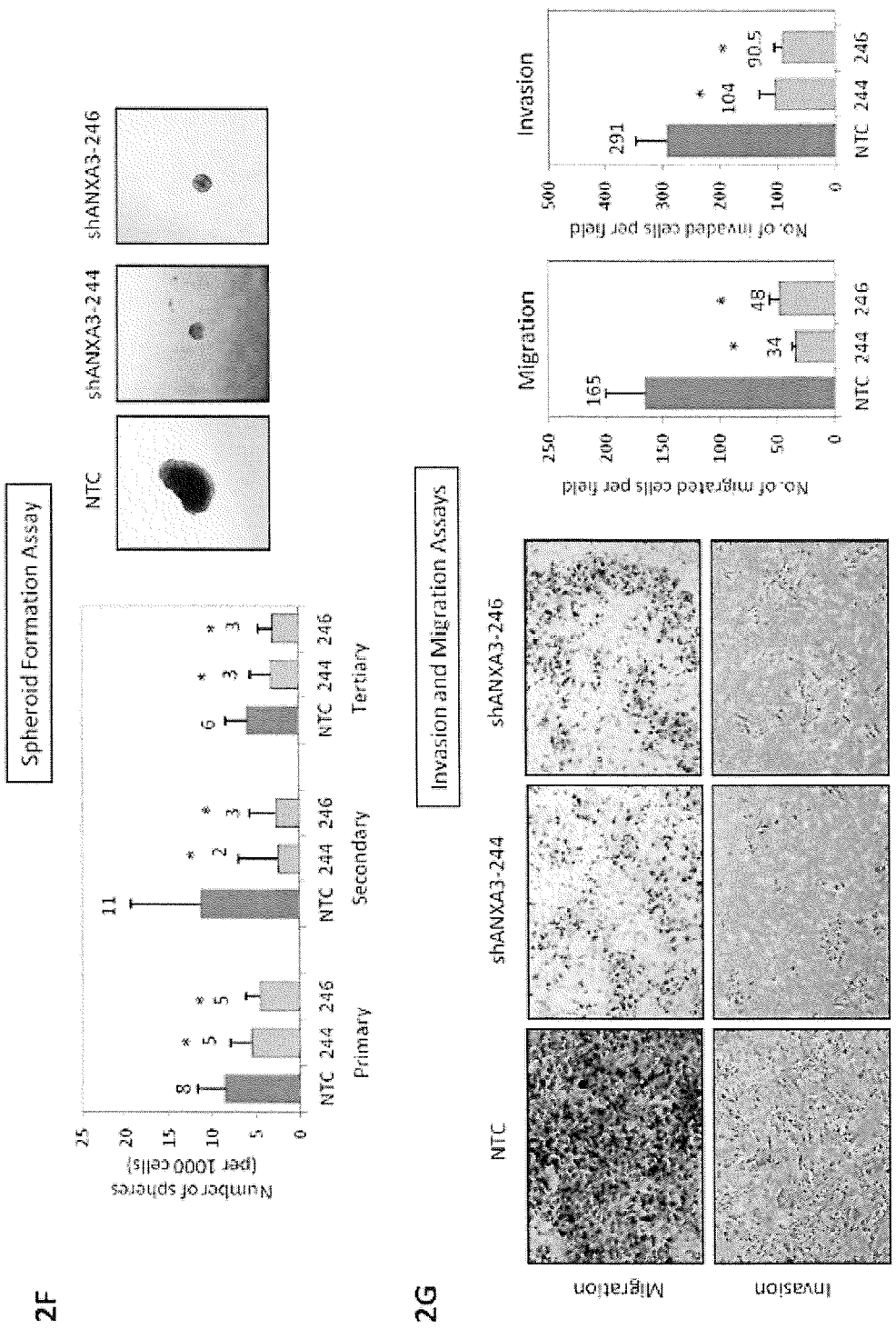
Figure 2:
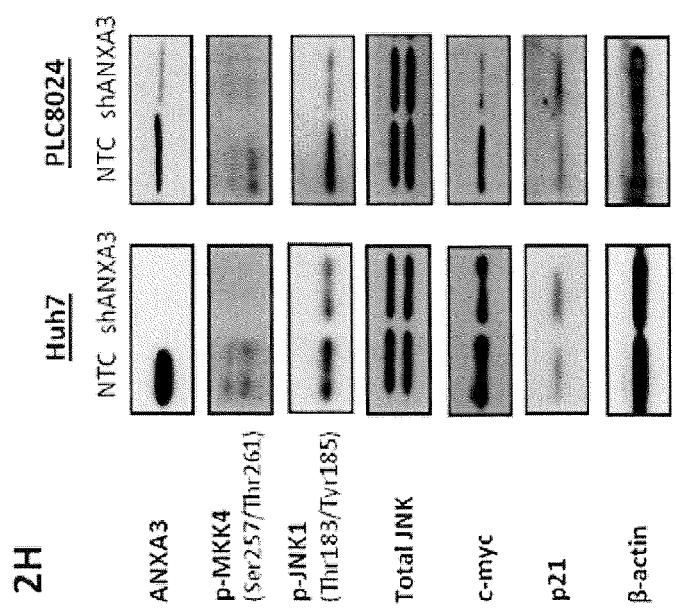

FIG. 2A shows qPCR, western blot and ELISA assay results for relative ANXA3 expression (qPCR) and secretory ANXA3 levels (ELISA) following lentiviral transduction using shRNA (clones 244 and 246) that target ANXA3 in Huh7 HCC cells. FIG. 2B shows results of a foci formation assay for NTC, shANXA3-244, and shANXA3-246. FIG. 2C shows results of a capillary tube formation assay for NTC, shANXA3-244, and shANXA3-246. Human umbilical vein endothelial cells (HUVEC) were treated with conditioned media collected from ANXA3 suppressed cells and its respective control. FIG. 2D shows tumor initiation in vivo by subcutaneous implantation in immunodeficient nude mice. ANXA3 repressed clones (shANXA3-244 and shANXA3-246) failed to give rise to tumor when implanted subcutaneously. FIG. 2E shows apoptosis analysis by flow cytometry in NTC and ANXA3 repressed clones, shANXA3-244 and shANXA3-246, treated with the apoptosis inducer, staurosporin (STS) or chemotherapeutic drugs, 5-fluorouracil and cisplatin. Increase in apoptotic and necrotic cells after STS treatment paralleled an increase in caspase 3 and PARP activity, as demonstrated by Western blot analysis. FIG. 2F shows results of a spheroid formation assay for ANXA3 repressed clones, shANXA3-244 and shANXA3-246, compared to NTC in serial passages. FIG. 2G shows results of invasion and migration assays for ANXA3 repressed clones, shANXA3-244 and shANXA3-246, and NTC. FIG. 2H shows western blot analysis for ANXA3, p-MKK4, p-JNK1, total JNK, c-myc, p21, and beta-actin (loading control) in PLC8024 and Huh7 cells, each cell line either NTC or ANXA3 repressed (shANXA3). Note: NTC stands for non-target control* stands for statistical significance in all panels of the Figures.

Figure 3:
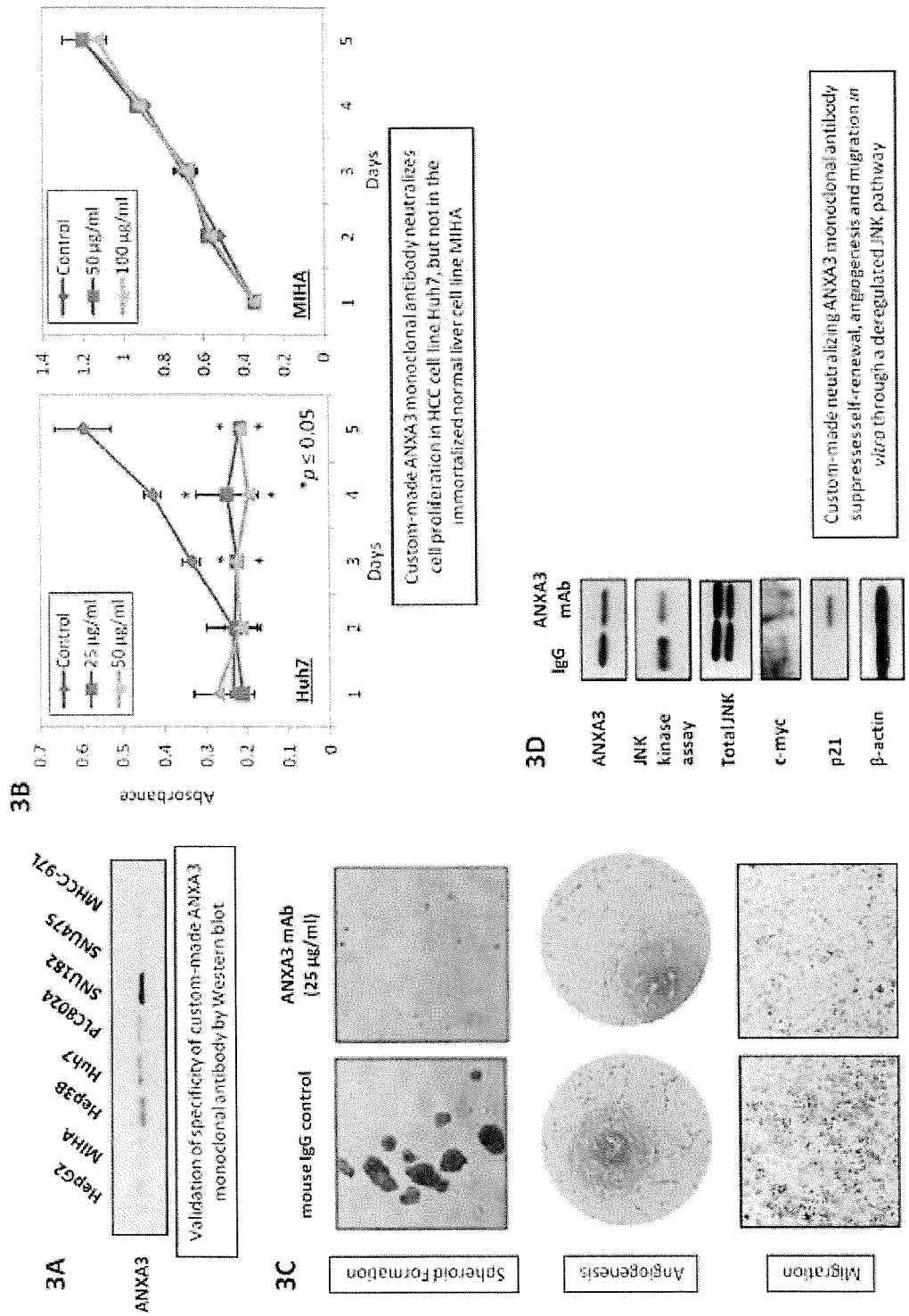
Figure 3:
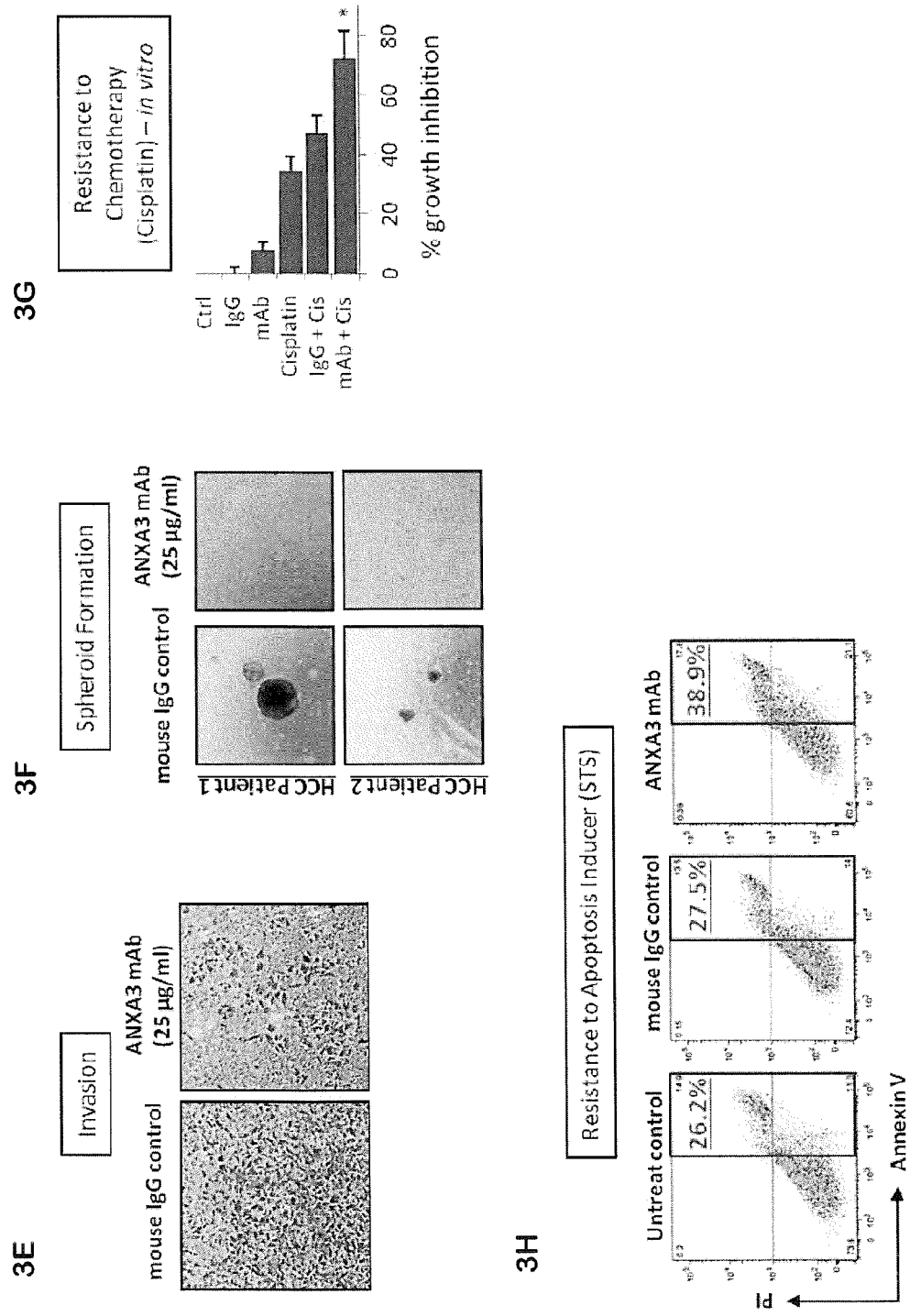

FIG. 3A shows western blot analysis of a panel of liver cell lines (HepG2, MIHA, Hep3B, Huh7, PLC8024, SNU182, SNU475, and MHCC-97L) utilizing a custom-made ANXA3 mouse monoclonal antibody for validation of the antibody's specificity. The antibody was developed through a paid service at Abmart, Shanghai. Note: inventors own the intellectual properties of the cell line/antibody produced at Abmart. FIG. 3B shows a graph of cell proliferation in Huh7 and MIHA cells following administration of the ANXA3 monoclonal antibody, administered at 25 µg/ml and 50 µg/ml concentration. FIG. 3C shows spheroid formation, angiogenesis assays, and migration assays for Huh7 cells following repression of ANXA3 by specific anti-human ANXA3 neutralizing antibody (25 µg/ml). FIG. 3D shows western blot analysis for ANXA3, JNK kinase, total JNK, c-myc, p21, and beta-actin (loading control) for HCC cells Huh7 following treatment with the neutralizing ANXA3 antibody. * stands for statistical significance in all panels of the Figures. FIG. 3E shows results of an invasion assay in Huh7 cells following administration of 25 µg/ml of the ANXA3 monoclonal antibody. FIG. 3F shows results of a spheroid formation assay in HCC patient samples (1 and 2) following administration of 25 µg/ml of the ANXA3 monoclonal antibody. FIG. 3G shows in vitro chemotherapy resistance analysis following administration of 25 µg/ml of the ANXA3 monoclonal antibody. FIG. 3H shows analysis for resistance to apoptosis inducer (STS) in untreated control, mouse IgG control, and ANXA3 mAb treated HCC cells.

Figure 4:
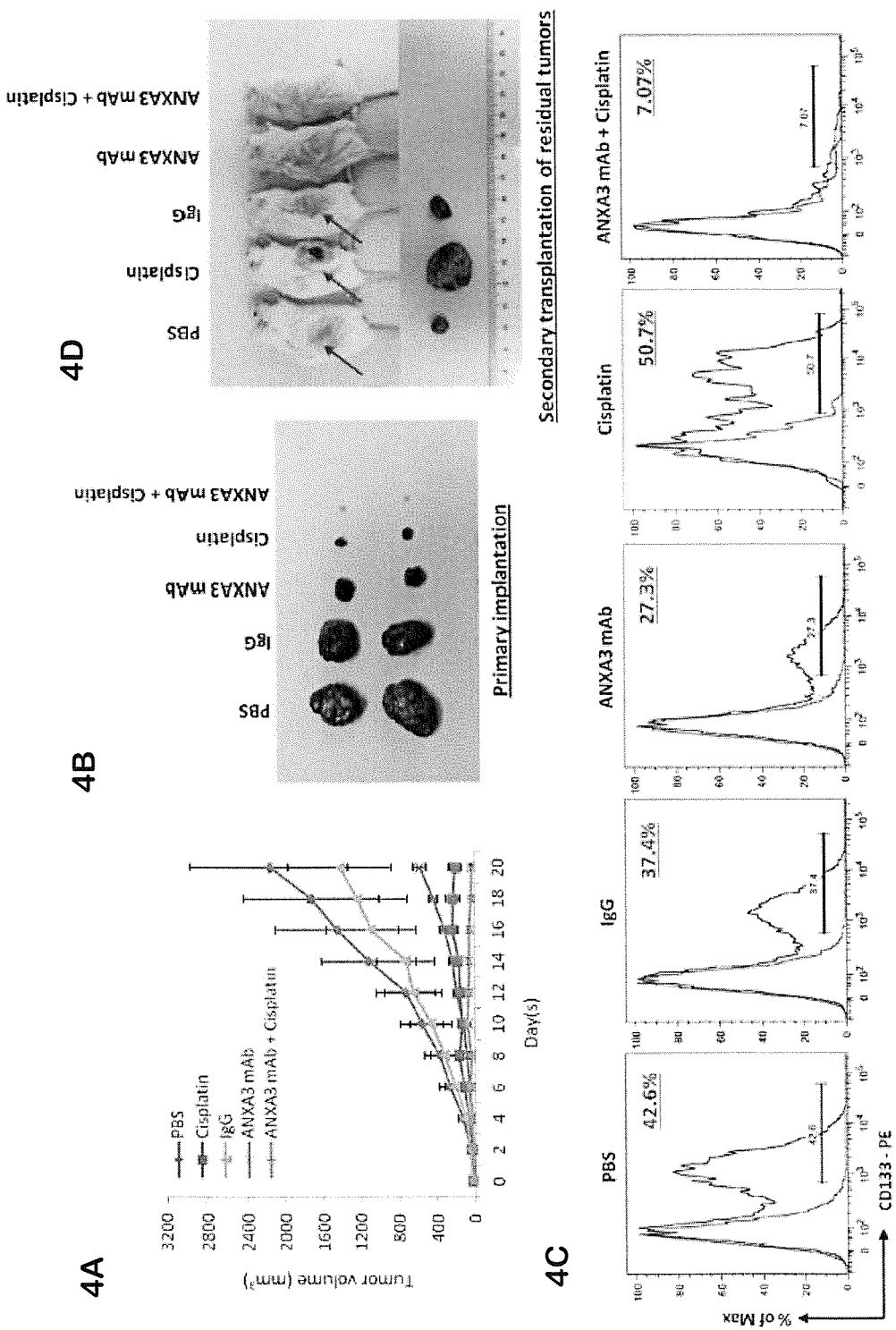

FIG. 4 shows (A) a graph of tumor volume and (B) a photo of tumors formed in immunodeficient NOD-SCID mice transplanted subcutaneously with HCC Huh7 cells or HCC primary cells and injected with PBS, mouse IgG control ANXA3 mAb, cisplatin or a combination of ANXA3 mAb and cisplatin over a period of 3 weeks. FIG. 4C shows respective flow cytometric analyses of the tumors. FIG. 4D shows tumor formation in mice following serial transplantation of residual tumor.

DETAILED DESCRIPTION

Endogenous and secretory ANXA3 is shown to be preferentially expressed in HCC cell lines and HCC clinical samples as compared to immortalized normal liver cell line and normal or non-tumor liver clinical samples. Furthermore, serum ANXA3 levels in healthy individuals and HCC patients of early and late stage HCC indicates that ANXA3 is upregulated in HCC patients. Most importantly, overexpression of secretory ANXA3 in HCC was significantly correlated with advanced tumor stage (p-value≤0.01). Lentiviral based shRNA knockdown in two separate HCC cell line models (Huh7 and PLC8024) shows that ANXA3 is critical in driving tumor initiation, self-renewal, invasion, migration, angiogenesis, and resistance to chemotherapy and apoptosis. Based on these findings, the present invention provides the use of ANXA3 as a novel biomarker for diagnosis or prognosis of HCC.

The present invention also provides antagonists of ANXA3 protein or mRNA as a therapeutic target for HCC treatment. ANXA3 antagonists as therapeutic agents for HCC include, but are not limited to, ANXA3 neutralizing antibody, shRNA binding to ANXA3 mRNA thereby inhibiting ANXA3 expression, siRNA binding to ANXA3 mRNA thereby inhibiting ANXA3 expression, and aptamers and small molecule chemicals that inhibit activity and/or expression of ANXA3 protein or mRNA.

Neutralization of ANXA3 using a newly developed custom-made monoclonal antibody led to inhibition of HCC cells to proliferate, invade, migrate, and induce capillary tube formation in vitro, through a deregulated JNK pathway. Thus, ANXA3 antagonists are of great potential clinical value as therapeutic agents for treatment of HCC.

The current invention also discloses the anti-tumor efficacy of short hairpin ribonucleic acid (shRNA) against ANXA3 on human HCC cells. The current invention demonstrates ANXA3 shRNA are able to retard the growth of proliferation, self-renewal, invasion and migration in vitro and in vivo, and sensitize HCC cells to chemotherapy and apoptosis.

The therapeutic agents for treatment of HCC as provided by the current invention can be administered alone or in combination with other HCC treatments. Chemotherapeutic drugs for treating HCC are well known in the art. The chemotherapeutic drugs which can be used in combination with the therapeutic agents of the present invention include, but are not limited to, cisplatin, doxorubicin, and/or 5-fluoruracil.

Definitions

To facilitate the understanding of the subject matter disclosed herein, a number of terms, abbreviations or other shorthand as used herein are defined below. Any term, abbreviation or shorthand not defined is understood to have the ordinary meaning used by a skilled artisan contemporaneous with the submission of this application.

The term "subject," as used herein, describes a mammal including, but not limited to, humans, apes, chimpanzees, orangutans, monkeys, dogs, cats, horses, pigs, sheep, goats, mice, rats, and guinea pigs.

The term "tumorigenesis," as used herein, refers to its ordinary meaning that is the development of malignant tumor.

Expression of ANXA3 at a similar level between two samples means that the concentration of ANXA3 present in the two samples is within 20% of each other.

Overexpression of ANXA3 in a test sample compared to ANXA3 expression in a control sample means that the concentration of ANXA3 in the test sample is more than 20% above the concentration of ANXA3 in the control sample.

"Specific binding" or "specificity" as it relates to binding between two molecules refers to the ability of a molecule, for example, an antibody, to detectably bind to its target site, for example, an epitope, presented on a target molecule of interest, for example, a target protein, while having relatively little detectable reactivity with other molecules or structures. Specificity can be relatively determined by binding or competitive binding assays. Specificity can be exhibited by, e.g., an about 10:1, about 20:1, about 50:1, about 100:1, 10,000:1 or greater ratio of affinity/avidity in binding to the specific target molecule versus nonspecific binding to other irrelevant molecules.

The term "nucleotide" refers to a nucleoside having one or more phosphate groups joined in ester linkages to the sugar moiety. Exemplary nucleotides include nucleoside monophosphates, diphosphates, and triphosphates. The terms "polynucleotide" and "nucleic acid molecule" are used interchangeably herein and refer to a polymer of nucleotides joined together by a phosphodiester linkage between 5' and 3' carbon atoms.

The terms "nucleic acid" or "nucleic acid sequence" encompass an oligonucleotide, nucleotide, polynucleotide, or a fragment of any of these, DNA or RNA of genomic or synthetic origin, which may be single-stranded or double-stranded and may represent a sense or antisense strand, peptide nucleic acid (PNA), or any DNA-like or RNA-like material, natural or synthetic in origin. As will be understood by those of skill in the art, when the nucleic acid is RNA, the deoxynucleotides A, G, C, and T are replaced by ribonucleotides A, G, C, and U, respectively.

As used herein, the term "RNA" or "RNA molecule" or "ribonucleic acid molecule" refers generally to a polymer of ribonucleotides. The term "DNA" or "DNA molecule" or deoxyribonucleic acid molecule" refers generally to a polymer of deoxyribonucleotides. DNA and RNA molecules can be synthesized naturally (e.g., by DNA replication or transcription of DNA, respectively). RNA molecules can be post-transcriptionally modified. DNA and RNA molecules can also be chemically synthesized. DNA and RNA molecules can be single-stranded (i.e., ssRNA and ssDNA, respectively) or multi-stranded (e.g., double stranded, i.e., dsRNA and dsDNA, respectively). Based on the nature of the invention, however, the term "RNA" or "RNA molecule" or "ribonucleic acid molecule" can also refer to a polymer comprising primarily (i.e., greater than 80% or, preferably greater than 90%) ribonucleotides but optionally including at least one non-ribonucleotide molecule, for example, at least one deoxyribonucleotide and/or at least one nucleotide analog.

As used herein, the term "nucleotide analog", also referred to herein as an "altered nucleotide" or "modified nucleotide," refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function.

As used herein, the term "RNA interference" ("RNAi") refers to a selective intracellular degradation of a target RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of endogenous target genes, such as ANXA3.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference.

As used herein, the term "short hairpin RNA" ("shRNA") refers to an RNA (or RNA analog) comprising between about 10-50 nucleotides (or nucleotide analogs) which self-hybridizes through complementary sequence to produce a hairpin structure and is capable of directing or mediating RNA interference.

As used herein, a siRNA or shRNA having a "sequence sufficiently complementary to a target mRNA sequence to direct target-specific RNA interference (RNAi)" means that the siRNA or shRNA has a sequence sufficient to trigger the destruction of the target mRNA (e.g., ANXA3 mRNA) by the RNAi machinery or process. "mRNA" or "messenger RNA" or "transcript" is single-stranded RNA that specifies the amino acid sequence of one or more polypeptides. This information is translated during protein synthesis when ribosomes bind to the mRNA.

The term "treatment" or any grammatical variation thereof (e.g., treat, treating, and treatment etc.), as used herein, includes, but is not limited to, ameliorating or alleviating a symptom of a disease or condition; reducing or delaying recurrence of a condition; reducing, suppressing, inhibiting, lessening, or affecting the progression and/or severity of an undesired physiological change or a diseased condition. For instance, treatment includes, for example, preventing, inhibiting, or slowing the rate of development of malignant HCC or conversion of a benign HCC into a malignant HCC; slowing the growth and/or proliferation of HCC; and reducing the size of malignant HCC tumor.

The term "effective amount," as used herein, refers to an amount that is capable of treating or ameliorating a disease or condition or otherwise is capable of producing an intended therapeutic effect. In certain embodiments, the effective amount enables a 5%, 10%, 20%, 30%, 40%, 50%, 75%, 90%, 95%, 99% or 100% reduction in the rate of formation of a malignant HCC tumor. In certain embodiments, the effective amount enables a 5%, 10%, 15%, 20%, 25%, 30%, 35%, or 40% reduction in the size of malignant HCC tumor.

Samples and/or ANXA3-specific binding agents may be arrayed on a solid support, or multiple supports can be utilized, for multiplex detection or analysis. "Arraying" refers to the act of organizing or arranging members of a library (e.g., an array of different samples or an array of devices that target the same target molecules or different target molecules), or other collection, into a logical or physical array. Thus, an "array" refers to a physical or logical arrangement of, e.g., biological samples. A physical array can be any "spatial format" or "physically gridded format" in which physical manifestations of corresponding library members are arranged in an ordered manner, lending itself to combinatorial screening. For example, samples corresponding to individual or pooled members of a sample library can be arranged in a series of numbered rows and columns, e.g., on a multi-well plate. Similarly, binding agents can be plated or otherwise deposited in microtitered, e.g., 96-well, 384-well, or 1536-well plates (or trays). Optionally, ANXA3-specific binding agents may be immobilized on a solid support.

As used herein, the term "expression construct" refers to a combination of nucleic acid sequences that provides for transcription of an operably linked nucleic acid sequence. As used herein, the term "operably linked" refers to a juxtaposition of the components described, wherein the components are in a relationship that permits them to function in their intended manner. In general, operably linked components are in contiguous relation.

Expression constructs of the invention will also generally include regulatory elements that are functional in the intended host cell in which the expression construct is to be expressed. Thus, a person of ordinary skill in the art can select regulatory elements for use in, for example, bacterial host cells, yeast host cells, mammalian host cells, and human host cells. Regulatory elements include promoters, transcription termination sequences, translation termination sequences, enhancers, and polyadenylation elements.

Diagnosis of HCC

One aspect of the present invention provides the use of ANXA3 as a biomarker for diagnosis of HCC. In one embodiment, the present invention provides a method for diagnosing the presence of HCC in a subject, the method comprising:

(a) obtaining a biological sample from the subject,
(b) detecting in the sample a level of expression for ANXA3, and
(c) comparing the expression level in (b) to a level of expression in a control,
(d) diagnosing the presence of HCC in the subject if ANXA3 is overexpressed in the biological sample from the subject with respect to the control sample or diagnosing the absence of HCC in the subject if ANXA3 is expressed at a similar or lower level in the biological sample from the subject with respect to the control sample.

In a further embodiment, the degree of ANXA3 overexpression, when compared to a control sample, corresponds to the rate of proliferation of HCC, wherein a higher degree of ANXA3 over-expression in the subject's sample indicates a higher rate of tumorigenesis of HCC in the subject.

In another embodiment, the present invention provides a method for predicting the risk of recurrence of HCC in a subject, wherein the subject has received treatment for HCC and as a result of the treatment, does not have detectable HCC cancer cells, the method comprising:

(a) obtaining a biological sample from the subject,
(b) detecting in the sample a level of expression for ANXA3, and
(c) comparing the expression level in (b) to a level of expression in a control, (d) diagnosing the recurrence of HCC in the subject if ANXA3 is overexpressed in the biological sample from the subject with respect to the control sample or diagnosing the absence of recurrence of HCC in the subject if ANXA3 is expressed at a similar level or lower in the biological sample from the subject with respect to the control sample.

The biological samples that can be used for the diagnosis of HCC in a subject according to the current invention include, but are not limited to, liver tissue, liver cells, and liver interstitial fluid, blood, serum, plasma, or urine. In an embodiment, the biological sample is obtained from a tumor, polyp, or cyst from a subject's liver, wherein overexpression of ANXA3 in the subject's sample, when compared to the control, indicates that the tumor, polyp, or cyst is associated with HCC.

The control can be obtained from a healthy individual who does not have HCC or any other cancer or disease, from an immortalized normal liver cell line, or from an individual successfully treated for HCC who is free from HCC.

The expression of ANXA3 can be determined based on mRNA or protein levels. Determination of ANXA3 expression can be made qualitatively, semi-quantitatively, or quantitatively. Sequences of ANXA3 proteins and mRNAs of a variety of mammalian species are publically available and can be obtained from, for example, GenBank database. For example, human ANXA3 has an amino acid sequence of SEQ ID NO: 4 (GenBank Accession No. CAG28576.1). A person of ordinary skill in the art, having the benefit of the present disclosure, can easily use ANXA3 sequence of a mammalian species of interest to practice the present invention.

Methods for determining ANXA3 expression level are well known in the art, including but not limited to, Western blots, Northern blots, Southern blots, enzyme-linked immunosorbent assay (ELISA), immunoprecipitation, immunofluorescence, radioimmunoassay, flow cytometry, immunocytochemistry, nucleic acid hybridization techniques, nucleic acid reverse transcription methods, nucleic acid amplification methods, and any combination thereof.

In one embodiment, the level of ANXA3 protein expression is determined by contacting the biological sample with an antibody that specifically recognizes, or specifically binds to, ANXA3 protein; and detecting the complex between the antibody and the ANXA3 protein. In preferred embodiments, the ANXA3 antibody does not recognize or bind to any other ANXA isomer. In certain embodiments, the level of ANXA3 expression can be determined by immunoassays including, but not limited to, radioimmunoassay, Western blot assay, ELISA, immunofluorescent assay, enzyme immunoassay, immunoprecipitation, chemiluminescent assay, immunohistochemical assay, dot blot assay, and slot blot assay.

A contacting step in the assay (method) of the invention can involve contacting, combining, or mixing the biological sample and the solid support, such as a reaction vessel, microvessel, tube, microtube, well, multi-well plate, or other solid support.

In a further embodiment, the diagnostic assay of the present invention is used in combination with other routine HCC diagnostic or screening techniques, such as X-rays, ultrasound, magnetic resonance imaging (MRI), needle biopsies, MRI-guided liver biopsies, surgical biopsies and/or other HCC biomarker screening assays.

In another aspect, the present invention includes kits comprising the required elements for detecting ANXA3. Preferably, the kits comprise a container for collecting a sample, such as liver tissue or blood sample from a patient, and an agent for detecting the presence of ANXA3 in the sample. The agent may be any binding agent specific for ANXA3, such as but not limited to antibodies and aptamers. The components of the kits can be packaged either in aqueous medium or in lyophilized form.

The methods of the invention can be carried out using a diagnostic kit for qualitatively or quantitatively detecting ANXA3 in a sample. By way of example, the kit can contain binding agents specific for ANXA3, for example, antibodies against ANXA3 labeled with an enzyme; and a substrate for the enzyme. The kit can also contain a solid support such as microtiter multi-well plates, standards, assay diluent, wash buffer, adhesive plate covers, and/or instructions for carrying out a method of the invention using the kit.

As indicated above, kits of the invention include reagents for use in the methods described herein, in one or more containers. The kits may include specific internal controls, and/or probes, buffers, and/or excipients, separately or in combination. Each reagent can be supplied in a solid form or liquid buffer that is suitable for inventory storage. Kits may also include means for obtaining a sample from a host organism or an environmental sample.

Kits of the invention can be provided in suitable packaging. As used herein, "packaging" refers to a solid matrix or material customarily used in a system and capable of holding within fixed limits one or more of the reagent components for use in a method of the present invention. Such materials include glass and plastic (e.g., polyethylene, polypropylene, and polycarbonate) bottles, vials, paper, plastic, and plastic-foil laminated envelopes and the like. Preferably, the solid matrix is a structure having a surface that can be derivatized to anchor an oligonucleotide probe, primer, molecular beacon, specific internal control, etc. Preferably, the solid matrix is a planar material such as the side of a microtiter well or the side of a dipstick. In certain embodiments, the kit includes a microtiter tray with two or more wells and with reagents including primers, probes, specific internal controls, and/or molecular beacons in the wells.

Kits of the invention may optionally include a set of instructions in printed or electronic (e.g., magnetic or optical disk) form, relating information regarding the components of the kits and/or how to make various determinations (e.g., ANXA3 levels, comparison to control standards, etc.). The kit may also be commercialized as part of a larger package that includes instrumentation for measuring other biochemical components.

Treatment of HCC and Inhibition of HCC Tumorigenesis

In another aspect, the present invention provides methods for inhibiting HCC tumorigenesis and/or treatment of HCC. In one embodiment, the method comprises administering to a subject in need of such treatment an effective amount of an ANXA3 inhibitor. In one embodiment, the present invention administers agents that specifically inhibit ANXA3 but do not substantially inhibit other ANXA isoforms.

In an embodiment, a subject in need of the treatment of the present invention has or is diagnosed of having HCC. In another embodiment, a subject in need of the treatment of the present invention is at risk of developing HCC tumorigenesis. In another embodiment, a subject in need of the treatment of the present invention has or is diagnosed of having tumorigenic HCC cells; however, no malignant HCC tumor has formed yet. In another embodiment, a subject in need of the treatment of the present invention has or is diagnosed of having pre-malignant HCC tumor cells, pre-cancerous HCC cells, and/or cancer stem cells. In another embodiment, a subject in need of the treatment of the present invention has ANXA3 overexpression in the liver. In an embodiment, the ANXA3-specific inhibitor is delivered to the liver of a subject in need of such treatment.

In an embodiment, the present invention provides a method for treating HCC and/or inhibiting HCC tumorigenesis. In an embodiment, the present invention can be used to treat or ameliorate primary HCC, in which cancer cells originated from liver tissue have not spread to other parts of the body. In another embodiment, the present invention can be used to treat metastatic HCC. In a specific embodiment, the present invention can be used to treat or ameliorate non-invasive and/or invasive HCC. In another embodiment, the present invention can be used to inhibit or prevent the formation of a malignant HCC tumor.

In certain embodiments, the present invention can be used to treat or ameliorate HCC, including clear cell type HCC, fibrolamellar HCC, sarcomatoid HCC, combined HCC-cholangiocarcinoma, and sclerosing HCC.

In an embodiment, the present invention excludes the administration of ANXA3 inhibitors that also inhibit the expression and/or activity of other ANXA isoforms. Non-limiting examples of such inhibitors include antibodies, binding partners, and/or aptamers that bind to ANXA protein isoform other than ANXA3; antisense nucleic acid molecules that inhibit the expression of ANXA protein isoform other than ANXA3; and compounds that inhibit ANXA protein isoform other than ANXA3.

ANXA3 Inhibitors

The present invention pertains to uses of ANXA3 inhibitors for preventing and/or inhibiting HCC tumorigenesis and for treating HCC. ANXA3 inhibitors useful according to the present invention include, but are not limited to, agents that inhibit ANXA3 activity; and agents that reduce or inhibit the expression of ANXA3, such as agents that inhibit the transcription, translation, and/or processing of ANXA3.

Agents that inhibit ANXA3 activity include, but are not limited to, ANXA3 antibodies, aptamers, ANXA3 binding partners, and small molecule inhibitors of ANXA3.

In one embodiment, the ANXA3 inhibitor is an antibody that binds specifically to ANXA3. In a certain embodiments the ANXA3 antibody is a monoclonal antibody. In a further embodiment, the ANXA3 monoclonal antibody binds to human ANXA3 and is a humanized monoclonal antibody. In certain embodiments, ANXA3 inhibitors include ANXA3 antibodies that bind specifically to ANXA3 proteins of non-human animals including, but not limited to, apes, chimpanzees, orangutans, monkeys, dogs, cats, horses, pigs, sheep, goats, mice, rats, and guinea pigs. A skilled artisan can easily construct ANXA3 antibodies to specifically target any ANXA3 protein publically known. In a specific embodiment, the ANXA3 inhibitor is an antibody that binds specifically to a human ANXA3 of SEQ ID NO: 4. In a further embodiment, the ANXA3 inhibitor is a monoclonal antibody that specifically binds to a portion of ANXA3 represented by SEQ ID NO: 1.

ANXA3 antibodies of the present invention can be in any of a variety of forms, including intact immunoglobulin molecules, fragments of immunoglobulin molecules such as ScFv, Fab, and similar fragments; multimers of immunoglobulin molecules (e.g., diabodies, triabodies, and bi-specific and tri-specific antibodies, as are known in the art; see, e.g., Hudson and Kortt, J. Immunol. Methods 231:177 189, 1999); fusion constructs containing an antibody or antibody fragment; and human or humanized immunoglobulin molecules or fragments thereof.

Antibodies within the scope of the invention can be of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes.

Antibodies of the present invention include polyclonal and monoclonal antibodies. The term "monoclonal antibody," as used herein, refers to an antibody or antibody fragment obtained from a substantially homogeneous population of antibodies or antibody fragments (i.e. the individual antibodies within the population are identical except for possible naturally occurring mutations that may be present in a small subset of the antibody molecules).

A monoclonal antibody composition is typically composed of antibodies produced by clones of a single cell called a hybridoma that secretes (produces) only one type of antibody molecule. The hybridoma cell is formed by fusing an antibody-producing cell and a myeloma or other self-perpetuating cell line. Such antibodies were first described by Kohler and Milstein, Nature, 1975, 256:495-497, the disclosure of which is herein incorporated by reference to the extent it is not inconsistent with the teachings herein. An exemplary hybridoma technology is described by Niman et al., Proc. Natl. Acad. Sci. U.S.A., 1983, 80:4949-4953. Other methods of producing monoclonal antibodies, a hybridoma cell, or a hybridoma cell culture are also well known. See e.g., Antibodies: A Laboratory Manual, Harlow et al., Cold Spring Harbor Laboratory, 1988; or the method of isolating monoclonal antibodies from an immunological repertoise as described by Sasatry, et al., Proc. Natl. Acad. Sci. USA, 1989, 86:5728-5732; and Huse et al., Science, 1981, 246:1275-1281. The references cited are hereby incorporated herein by reference to the extent it is not inconsistent with the teachings herein.

In some embodiments, ANXA3 inhibitors useful according to the present invention are agents that reduce or inhibit the expression of ANXA3, such as agents that inhibit the transcription, translation, and/or processing of ANXA3 mRNA.

In an embodiment, the ANXA3 inhibitor is an ANXA3 antisense polynucleotide. In an embodiment, the ANXA3 inhibitor is an antisense polynucleotide that targets human ANXA3 mRNA. In some embodiments, the ANXA3 antisense polynucleotides target ANXA3 mRNAs of non-human animals including, but not limited to, apes, chimpanzees, orangutans, monkeys, dogs, cats, horses, pigs, sheep, goats, mice, rats, and guinea pigs. A skilled artisan would readily appreciate that based on the teaching of the current invention the antisense polynucleotides can be designed to target any ANXA3 mRNAs publically known.

In some embodiments, the ANXA3 inhibitor is a shRNA having a sequence sufficiently complementary to a target ANXA3 mRNA sequence to direct target-specific RNA interference (RNAi). In certain embodiments, the ANXA3 inhibitor is a siRNA having a sequence sufficiently complementary to a target ANXA3 mRNA sequence to direct target-specific RNA interference (RNAi). In some embodiments, the ANXA3 inhibitor is shRNA or siRNA having a sequence sufficiently complementary to a target human ANXA3 mRNA sequence (such as mRNA having a corresponding cDNA sequence of SEQ ID NO: 5, GenBank Accession No. NM_005139.2) to direct target-specific RNA interference.

In certain embodiments shRNA of the current invention have RNA sequences complementary to the following cDNA sequence:

```
                                                            (SEQ ID NO: 2)
CCGGCCAGATCAGAAATTGACCTTTCTCGAGAAAGGTCAATTTCTGAT
CTGGTTTTG,
or (SEQ ID NO: 3)
CCGGGTAAGAGATTATCCAGACTTTCTCGAGAAAGTCTGGATAATCTCT
TACTTTTG.
```

In a further embodiment, the pharmaceutical agent of the current invention comprises a combination of shRNA having RNA sequences complementary to sequences represented by SEQ ID NO: 2 and SEQ ID NO: 3.

Examples of ANXA3 antisense polynucleotides include, but are not limited to, single-stranded DNAs and RNAs that bind to complementary target ANXA3 mRNA and inhibit translation and/or induce RNaseH-mediated degradation of the target transcript; siRNA oligonucleotides that target or mediate ANXA3 mRNA degradation; ribozymes that cleave ANXA3 mRNA transcripts; and nucleic acid aptamers and decoys, which are non-naturally occurring oligonucleotides that bind to and block ANXA3 protein targets in a manner analogous to small molecule drugs.

The present invention also contemplates vectors (e.g., viral vectors) and expression constructs comprising the nucleic acid molecules useful for inhibiting ANXA3 expression and/or activity. In an embodiment, the vector comprises a shRNA or siRNA that targets ANXA3 mRNA. In another embodiment, the vector comprises a nucleic acid molecule encoding an ANXA3 antibody.

An expression construct of the invention can comprise a promoter sequence operably linked to a polynucleotide sequence encoding an ANXA3 inhibitor, for example, ANXA3 antibody. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

Therapeutic Compositions and Formulations

The present invention further provides therapeutic compositions that contain an effective amount of a therapeutic agent of the current invention (ANXA3 inhibitors or antagonists) and a pharmaceutically acceptable carrier or adjuvant.

The therapeutic composition of the current invention can comprise an agent selected from the group consisting of an antibody binding to a peptide having the amino acid sequence ENRWGTDEDK (SEQ ID No: 1), shRNA having a sequence complementary to the cDNA sequence of CCG-GCCAGATCAGAAATTGACCTTTCTCGAGAAAGGT-CAATTTCTGATCTGGTTTTT G (SEQ ID NO: 2), shRNA having a sequence complementary to the cDNA sequence of CCGGGTAAGAGATTATCCAGACTTTCTCGA-GAAAGTCTGGATAATCTCTTACTTTTT G (SEQ ID NO: 3), and combinations thereof.

The therapeutic composition can be formulated in a variety of forms. These include for example, solid, semisolid, and liquid dosage forms, such as tablets, pills, powders, liquid solutions or suspensions, suppositories, and injectable and infusible solutions. The preferred form depends on the intended mode of administration and therapeutic application.

In a preferred embodiment, the composition is formulated in accordance with routine procedures as a pharmaceutical composition adapted for local injection administration to human beings. Typically, compositions for local injection administration are solutions in sterile isotonic aqueous buffer. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile water for injection or saline can be provided so that the ingredients may be mixed prior to administration.

The present invention also provides for a therapeutic method by administering therapeutic or pharmaceutical compositions in a form that can be combined with a pharmaceutically acceptable carrier. In this context, the compound may be, for example, isolated or substantially pure. The term "carrier" refers to a diluent, adjuvant, excipient, or vehicle with which the compound is administered. Such pharmaceutical carriers can be sterile liquids, such as water and oils, including those of petroleum oil such as mineral oil; vegetable oil such as peanut oil, soybean oil, and sesame oil; animal oil; or oil of synthetic origin.

Suitable carriers also include ethanol, dimethyl sulfoxide, glycerol, silica, alumina, starch, sorbitol, inositol, xylitol, D-xylose, manniol, powdered cellulose, microcrystalline cellulose, talc, colloidal silicon dioxide, calcium carbonate, magnesium cabonate, calcium phosphate, calcium aluminium silicate, aluminium hydroxide, sodium starch phosphate, lecithin, and equivalent carriers and diluents. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The therapeutic composition, if desired, can also contain minor amounts of wetting or emulsifying agents, or pH buffering agents.

The amount of active ingredient that may be combined with the carrier materials to produce a single dosage form will vary, depending on the type of the condition and the subject to be treated. In general, a therapeutic composition contains from about 5% to about 95% active ingredient (w/w). More specifically, a therapeutic composition contains from about 20% (w/w) to about 80% or about 30% to about 70% active ingredient (w/w).

The therapeutic agents of the invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the present invention.

The therapeutic or pharmaceutical compositions of the present invention can also be formulated as neutral or salt forms. Pharmaceutically acceptable salts include, but are not limited to, hydrochloric, phosphoric, acetic, oxalic, sodium, potassium, ammonium, calcium, ferric hydroxides, isopropylamine, and triethylamine salts.

While it may be possible for an ANXA3 antibody to be administered as a raw composition, it is also possible to present them as a pharmaceutical formulation. Accordingly, a pharmaceutical formulation comprising an ANXA3 antibody or a pharmaceutically acceptable salt, ester, prodrug or solvate thereof, together with one or more pharmaceutically acceptable carriers thereof and optionally one or more other therapeutic ingredients is provided. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions may be manufactured in a manner that is itself known, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intra-articular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a peptide or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active peptide doses.

ANXA3 antibody composition may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the monoclonal antibody composition may also be formulated as a depot preparation. Such long acting formulations may be administered by implantation (for example subcutaneously or intramuscularly) or by intramuscular injection. Thus, for example, the peptides may be formulated with suitable polymeric or hydrophobic materials (for example an emulsion in an acceptable oil) or ion exchange resins, or as sparingly soluble derivatives, for example, as a sparingly soluble salt.

For buccal or sublingual administration, the monoclonal antibody composition may take the form of tablets, lozenges, pastilles, or gels formulated in conventional manner. Such compositions may comprise the active ingredient in a flavored basis such as sucrose and acacia or tragacanth.

The composition may also be formulated in rectal compositions such as suppositories or retention enemas, e.g., containing conventional suppository bases such as cocoa butter, polyethylene glycol, or other glycerides.

Preferred unit dosage formulations are those containing an effective dose, as herein below recited, or an appropriate fraction thereof, of the monoclonal antibody.

The amount of the monoclonal antibody for a single dosage form above or in combination with carrier materials will vary depending upon the severity of the liver cancer and particular mode of administration. The phrase "the therapeutic use" is intended to qualify the amount of monoclonal antibody used in its treatment of liver cancer. This amount will be used to treat or reduce the tumor size for HCC tumors.

Route of Administration

The therapeutic agents and compositions of the present invention can be administered to the subject being treated by standard routes, including oral, or parenteral administration including intravenous, intramuscular, and intraspinal injection, infusion, and electroporation, as well as co-administration as a component of any medical device or object to be inserted (temporarily or permanently) into a subject.

In some embodiments, the methods disclosed herein include contacting a malignant HCC tumor or malignant HCC tumor cells with an effective amount of an ANXA3 inhibitor. In some embodiments, the ANXA3 inhibitor comprises a polynucleotide (including recombinant expression vectors encoding ANXA3 antisense RNA, ANXA3 shRNA, or intracellular ANXA3 antibodies). The amount of the therapeutic or pharmaceutical composition of the present invention effective in the treatment of HCC and/or inhibition of HCC tumorigenesis will depend on a variety of factors, such as the route of administration and the seriousness of the condition, and should be decided according to the judgment of the practitioner and each patient's circumstances. In general, the dosage ranges from about 0.01 µg/kg to about 10 mg/kg, about 0.01 µg/kg to about 1 mg/kg, about 0.01 µg/kg to about 100 µg/kg, about 0.01 µg/kg to about 10 µg/kg, or about 0.01 µg/kg to about 1 µg/kg. Such a unit dose may be administered once to several times (e.g. two, three and four times) every two weeks, every week, or every day.

In one embodiment, the therapeutic agents and compositions of the present invention and any second therapeutic agent are administered simultaneously or sequentially to the patient, with the second therapeutic agent being administered before, after, or both before and after treatment with the therapeutic agents of the present invention. Sequential administration may involve treatment with the second therapeutic agent on the same day (within 24 hours) of treatment with the subject compound. Sequential administration may also involve continued treatment with the second therapeutic agent on days that the subject compound is not administered.

Method of Screening for ANXA3 Inhibitors

In an embodiment, the invention provides a method of screening for ANXA3 inhibitors as useful candidates for treatment of HCC tumorigenesis or HCC, the method comprising obtaining a potential ANXA3 inhibitor; contacting a tumorigenesis or cancerous HCC cell with the potential ANXA3 inhibitor, determining whether growth or proliferation of the tumorigenesis or cancerous HCC cell is slowed by the presence of the potential ANXA3 inhibitor; and, if so, identifying the potential ANXA3 inhibitor as an ANXA3 inhibitor which can be a useful candidate for treatment of HCC tumorigenesis or HCC.

Various assays for identifying inhibitors of ANXA3 inhibitors are well known to a person of ordinary skill in the art and such assays are within the purview of the current invention.

It should be understood that in addition to the ingredients particularly mentioned above, the formulations may include other agents conventional in the art having regard to the type of formulation in question, for example those suitable for oral administration may include flavoring agents.

The following examples show various defined uses of ANXA3 monoclonal antibodies. The examples are illustrative of the practices of the invention, and not meant to be a limitation thereof.

EXAMPLES

Materials and Methods

Patient Specimens

All clinical specimens used in this study were collected from HCC patients who underwent surgical resection of tumor tissues at the Sun Yat-Sen University Cancer Center (Guangzhou, China). Patients' consent and approval from the Institute's Research Ethics Committee was obtained before clinical material collection for research purposes. Paired adjacent non-tumor tissues were also collected. The patients had received no previous local or systemic treatment prior to operation. For proteomic analysis of ANXA3 expression by Western blot, a total of 43 matched non-tumor and HCC samples were used. For serum ANXA3 expression analysis by ELISA, a total of 60 serum samples collected from HCC patients representative of Stage I and II or Stage III and IV (n=30 per group) were used. Serum samples from 32 healthy donors who were hepatitis B surface antigen (HBsAg) negative were also used for comparison analysis. Serum samples were frozen at −80° C. prior to use. Tumor and adjacent non-tumor liver tissues from HCC patients were collected and snapped frozen in liquid nitrogen and stored at −80° C. prior to use. Clinical and pathological data including serum AFP level of all patients and control subjects were prospectively collected Cell Lines Human HCC cell lines Hep3B, Huh7, HepG2, SNU182 and SNU475 were purchased from the American Type Culture Collection (ATCC). HCC cell line MHCC-97L was obtained from Liver Cancer Institute of Fudan University (Shanghai, China). HCC cell line PLC8024 was obtained from the Institute of Virology, Chinese Academy of Medical Sciences (Beijing, China). Immortalized normal liver cell line MIHA was provided by Dr. J. R. Chowdhury, Albert Einstein College of Medicine (New York). All cell lines were cultured in DMEM medium (Invitrogen) supplemented with 10% fetal bovin serum (Invitrogen), penicillin (500 U/ml) and streptomycin (500 µg/ml).

RNA Extraction and Real-Time Quantitative RT-PCR

Total RNA was isolated with Trizol reagent (Invitrogen) and cDNA was synthesized using the Advantage RT-for-PCR kit (Clontech). For each qPCR reaction, equal amounts of cDNA were mixed with Power SYBR Green PCR master mix (Applied Biosystems) and 5 pmol of forward and reverse primers specific for ANXA3 (ANXA3 F 5'-GCAG-GAGGAAGGGGTGCGGT-3' sequence (SEQ ID NO:6) and ANXA3 R 5'-TCCAAAGCGCGGTGGGGGAA-3' sequence (SEQ ID NO:7)). β-actin was amplified as an internal control. qPCR was conducted at 50° C. for 2 min, 95° C. for 10 min, followed by 40 cycles of 95° C. for 15 s and 60° C. for 1 min. Specificity was verified by melt curve analysis. Incorporation of the SYBR Green dye into PCR products was monitored in real time with an ABI 7900HT Sequence Detection System and SDS 1.9.1 software (Applied Biosystems); then subsequently analyzed using RQ Manager 1.2 software (Applied Biosystems), thereby allowing the threshold cycle ($C_T$) at which exponential amplification of the products began to be determined. The amount of target cDNA was calculated relative to that of β-actin cDNA.

Protein Extraction and Western Blotting

Total proteins were extracted by homogenizing cell pellets or snapped frozen patient tissue samples in RIPA buffer (Sigma) supplemented with 1× protease inhibitor cocktail (Roche) and 1 mM PMSF. Quantified protein lysates (20 m/lane) were resolved on SDS-PAGE, transferred onto PVDF membrane (Millipore) and probed with rabbit ANXA3 (Abcam) or mouse anti-human beta-actin (Sigma-Aldrich) antibody, followed by incubation with secondary HRP-conjugated antibodies. Blots were visualized by chemiluminescence (Amersham). ImageJ software was used to quantify intensity of each ANXA3 band relative to β-actin. A cut-off value of T/N>2 was used to determine ANXA3 overexpression in HCC patients.

Determination of ANXA3 Levels in Subject Serum

Serum ANXA3 protein levels were measured by a specific human ANXA3 ELISA kit (Cusabio) in 60 HCC patients and 32 healthy individuals, according to manufacturer's instructions. The median and mean levels of serum ANXA3 in healthy subjects were 1.29 ng/ml and 2.39 ng/ml, respectively (range, 0 to 9.37 ng/ml). The median and mean concentrations of serum ANXA3 in HCC patients were 5.73 ng/ml and 9.60 ng/ml, respectively (range, 0 to 109.46 ng/ml).

Establishment of ANXA3 Knockdown by shRNA Lentiviral Transduction

ANXA3 shRNA lentiviral knockdown (Sigma-Aldrich, NM_005139) were packaged using MISSION Lentiviral Packaging Mix (Sigma-Aldrich). Stable clones were selected using puromycin. Cells were infected with lentiviral media at a multiplicity of infection of 10, in the presence of 8 mg/ml polybrene (Sigma-Aldrich) overnight in a 37° C. incubator. Non-target control (NTC) was used as a control. Knockdown efficiency was confirmed by qPCR and Western blot as described above.

Cell Proliferation Assay

Cellular proliferation was determined using XTT cell proliferation assay (Roche Diagnostics) or foci formation assay. For the XTT cell proliferation assay, $2 \times 10^3$ cells were seeded to a 96-well plate in 100 µl DMEM medium containing 1% FBS either with or without ANXA3 antibody (25 µg/ml). For every 24 hrs, the medium was added with 50 µl XTT labeling mixture and incubated for 3 hrs at 37° C. Absorbance was measured with a spectrophotometer (Tecan Sunrise) at 492 nm with a reference wavelength of 630 nm. Each data point represented results from 3 independent experiments, each performed in triplicates. For foci formation assay, $5 \times 10^3$ cells were seeded to a 6-well plate in 1 ml complete DMEM medium and allowed to grow for 14 days. Cell proliferation was assessed by a colorimetric assay using crystal violet (Sigma Chemical), a cytochemical stain that binds to chromatin.

Spheroid Formation Assay

Single HCC cells were cultured in 300 µl of serum-free DMEM/F12 medium (Invitrogen), supplemented with 4 µg/ml insulin (Sigma-Aldrich), B27 (1:50; Invitrogen), 20 ng/ml recombinant EGF (Sigma-Aldrich), 10 ng/ml recombinant basic FGF (Invitrogen), 500 U/ml penicillin (Invitrogen) and 500 µg/ml streptomycin (Invitrogen). Cells were cultured in suspension in poly-HEMA-coated 24-well plates. Cells were replenished with 30 µl of supplemented medium every second day. To propagate spheres in vitro, spheres were collected by gentle centrifugation and were dissociated to single cells using TrypLE Express (Invitrogen). Following dissociation, trypsin inhibitor (Sigma-Aldrich) was used to neutralize the reaction, and cells were cultured to generate spheres of the next generation as described above.

Matrigel Invasion and Transwell Migration Assays

Invasion and migration assays were performed in 24-well BioCoat Matrigel Invasion Chambers (BD Biosciences) according to manufacturer's instructions or a 24-well milicell hanging insert (Millipore). In brief, $1 \times 10^5$ cells were added to the top chamber, and 10% FBS in DMEM was added to the bottom chamber as a chemoattractant. After 48 hrs incubation at 37° C., the number of cells that invaded through the membrane (migration) or Matrigel (invasion) was fixed in methanol, stained with crystal violet, counted in 10 random fields under a 20× objective lens and imaged using imaging software.

Capillary Tube Formation Assays in HUVEC

Huh7 and PLC8024 HCC cells with or without ANXA3 repressed (or NTC) or in the presence of ANXA3 antibody (or mouse IgG isotype control) were cultured in serum-free medium for 24 hrs. Conditioned media were collected and filtered for subsequent treatment of human umbilical vein endothelial cells (HUVECs) (Invitrogen). A total of $1 \times 10^4$ HUVECs were seeded into 96-well plate pre-coated with 50 µl Matrigel (BD Biosciences) and co-cultured with conditioned medium for 4 hrs. The formation of tube-like structures was examined and photographed using an inverted microscope.

Apoptosis Analysis by Flow Cytometry

Cells were treated with cisplatin (5 µg/ml) or 5-fluorouracil (150 µg/ml) for 48 hrs, apoptosis inducer staurosporin (STS, 1 µg/ml) for 6 hrs. Cells would then be subsequently harvested and stained in binding buffer, propidium iodide (PI) and FITC-conjugated Annexin V as provided by the Annexin-V FLUOS Staining Kit (Roche Diagnostics) according to manufacturer's instructions. Analysis was determined by a FACS Canto II (BD Biosciences) and FlowJo software (Tree Star, Inc.).

In Vivo Tumorigenicity Assays

The study protocol was approved by and performed in accordance with the Committee of the Use of Live Animals in Teaching and Research at the University of Hong Kong. For ANXA3 transplantation studies, lentiviral-delivered shRNA ANXA3 and NTC cells were injected subcutaneously into the flank of four-week old nude mice in complete medium. Each group contained five animals. Cryosections (5 µm thick) were stained with H&E and used for immunohistochemical analysis. Animals that were injected with tumor cells but showed no sign of tumor burden were generally terminated three months after tumor cell inoculation, and animals were opened up at the injection sites to confirm that there was no tumor development.

Generation of ANXA3 Neutralizing Monoclonal Antibody

The ANXA3 monoclonal antibody used in this invention was generated in collaboration with Abmart, Shanghai. The inventors own the intellectual properties of the cell line/antibody produced by Abmart. To generate the ANXA3 monoclonal antibody, a synthetic peptide targeted at ENRWGTDEDK (SEQ ID NO: 1) of the ANXA3 protein was used as an immunogen to generate the antibodies. Applicant intends to make a deposit of the ANXA3 monoclonal antibody with an internationally recognized depository in accord with the terms of the Budapest Treaty.

Statistical Analyses

All statistical analyses were performed using PASW Statistics 18.0 (SPSS Inc.), with the exception of the significance in bar graphs, in which case analyses were performed by applying the independent t-test using Microsoft Office Excel software (Microsoft Corp.). A p-value less than 0.05 was considered statistically significant.

Mouse Hybridoma cell line ANXA3-3M1-Hyb is deposited with American Type Culture Collection (ATCC), P.O. Box 1549, Manassas, Va. 20108, as accession number PTA-121826 under conditions that assure that access to the cultures will be available during the pendency of this patent application to one determined by the Commissioner of Patents and Trademarks to be entitled thereto under 37 CFR 1.14 and 35 U.S.C. 122. The deposit will be available as required by foreign patent laws in countries wherein counterparts of the subject application, or its progeny, are filed. However, it should be understood that the availability of a deposit does not constitute a license to practice the subject invention in derogation of patent rights granted by governmental action.

Example 1

Preferential Expression of Endogenous and Secretory ANXA3 in HCC Cell Lines and Clinical Samples Western blot and ELISA were carried out to evaluate the endogenous and secretory expression of ANXA3, respectively. Endogenous and secretory ANXA3 expression, at both genomic and proteomic levels, was first examined in a panel of liver cell lines by real-time qPCR, Western blot and ELISA. As compared with the immortalized normal liver cell line MIHA, all four HCC cell lines (Huh7, Hep3B, PLC8024 and SNU182) expressed significantly more ANXA3 expression (FIG. 1A).

Western blot analysis on 43 paired primary HCC and their corresponding non-tumor tissues revealed a frequent up-regulation of ANXA3 expression in HCC tissue. A cut-off value of T/N>2 was used to determine ANXA3 overexpression in HCC patients. Twenty two (51.2%) of the 43 cases examined showed more than two-fold increase in ANXA3 expression in HCC as compared with their non-tumor counterpart (FIG. 1B). Secretory ANXA3 expression was evaluated in early (Stages I and II) HCC patients (n=30), late (Stages III and IV) HCC patients (n=30) as well as healthy normal individuals (n=32). Serum ANXA3 levels were significantly up-regulated in HCC patients compared with normal healthy individuals (p-value≤0.05). A stepwise increase in secretory ANXA3 was observed from normal patients to early stage HCC (p<0.05) and then to advanced stage HCC (p<0.001). Among the HCC patients, higher serum ANXA3 levels were significantly correlated with advanced tumor stages (p-value≤0.001) (FIG. 1C). Serum ANXA3 has a better diagnostic value as compared to the commonly used AFP. The measurement of a combination of serum AFP and ANXA3 provides an even more specific and sensitive diagnosis for HCC. (FIGS. 1D and 1E)

Example 2

Role of ANXA3 in HCC Initiation and Development

The functional role of ANXA3 in driving tumor initiation, self-renewal, invasion, migration, angiogenesis and resistance to apoptosis and chemotherapy was investigated by a lentiviral based shRNA knockdown approach to SEQ ID. NOs: 2 and 3.

The effect of ANXA3 on tumor initiation was investigated by tumorigenicity assay in immunodeficient nude mice. ANXA3 repressed clones in Huh7 and PLC8024 HCC cells failed to give rise to tumors when implanted subcutaneously in immunodeficient nude mice.

The effect of ANXA3 on self-renewal was investigated by a spheroid formation assay in vitro. ANXA3 knockdown resulted in a diminished ability of Huh7 and PLC8024 HCC cells to initiate spheroid formation and propagate in serial secondary and tertiary passages (p-value<0.05).

The effect of ANXA3 on invasion and migration was evaluated using Matrigel invasion and transwell migration assays, respectively. ANXA3 knockdown resulted in a diminished ability of Huh7 and PLC8024 HCC cells to invade and migrate in vitro (p-value<0.05).

The effect of ANXA3 to induce capillary tube formation in HUVEC cells was investigated with conditioned media collected from Huh7 and PLC8024 HCC cells with or without ANXA3 stably repressed. ANXA3 knockdown resulted in a diminished capillary tube-forming ability in HUVECs. (p-value<0.05).

Example 3

ANXA3 Regulates Both Cancer and Stem Cell-Like Properties in HCC

Functional studies involving lentiviral-based knockdown approach found ANXA3 to regulate both cancer and stem cell-like properties. The inventors generated stably repressed ANXA3 Huh7 HCC cells using a shRNA lentiviral knockdown system. Of the 5 ANXA3 shRNA clones, 244 and 246 showed the most dramatic ANXA3 inhibition compared with non-target control, as confirmed by qPCR and Western blot, and thus were chosen for further studies (FIG. 2A). Note that endogenous ANXA3 repression also resulted in a diminished level of secretory ANAX3 produced, as detected by ELISA (FIG. 2A). Repressing ANXA3 expression in Huh7 resulted in a significant decrease in the efficiency of the cells to form foci when compared with NTC (FIG. 2B; * p-value<0.05). Conditioned medium collected from Huh7 cells with or without ANXA3 repressed showed that ANXA3 knockdown would result in a decreased ability of the cells to stimulate capillary tube structure formation in HUVECs when compared to conditioned medium collected from NTC cells (FIG. 2C; * p-value<0.05). This finding was further supported in an in vivo nude mouse model in which the tumor formation ability of ANXA3 repressed clone was significantly repressed when compared with NTC cells (FIG. 2D). Note similar observations were consistently observed in both ANXA3 knockdown clones (244 and 246), as well as in another HCC cell line model, PLC8024.

Example 4

Determination of Effects of ANXA3 on Resistance to Apoptosis and Chemotherapy

The effect of ANXA3 on resistance to apoptosis and chemotherapy was investigated by Annexin V-PI staining followed by flow cytometry analysis. To investigate whether ANXA3 expression in HCC confers enhanced resistance to chemotherapy and apoptosis, Huh7 cells with or without ANXA3 repressed were treated with the apoptosis inducer staurosporin (STS) or chemotherapeutic reagents, 5-fluorouracil (5-FU) or cisplatin, in vitro and analyzed for apoptotic/necrotic cells by flow cytometry. Huh7 cells with ANXA3 repressed were found to be more sensitive to STS and chemotherapeutic drugs than Huh7 NTC cells, as evident by their increased apoptotic rates (FIG. 2E). STS-induced apoptosis increased from 43.72% in control cells to 53.58 and 52.3% in ANAX3 repressed clones, through a mechanism involving a deregulated caspase 3/PARP pathway. 5-fluorouracil-induced apoptosis increased from 30.1% in control cells to 39.4 and 55.51% in ANXA3 repressed clones.

Cisplatin-induced apoptosis increased from 26.73% in control cells to 38.4 and 41.1% in ANXA3 repressed clones. Upon stable ANXA3 knockdown in Huh7 and PLC8024 HCC cells, HCC cells became less resistant to the apoptosis inducer, staurosporin (STS) and chemotherapy, 5-fluorouracil and cisplatin, resulting in a significant increase in apoptotic/necrotic cells.

The inventors also examined the effect of ANXA3 on the ability of HCC cells to grow as spheroids in non-adherent, serum-free, growth factor-supplemented conditions, suggestive of self-renewal. Huh7 cells with ANXA3 repressed had a diminished ability to initiate spheroid formation as well as to clonally expand in subsequent serial propagations, showing limited growth potential (FIG. 2F; * p-value<0.05). In addition, the inventors also examined the effect of ANXA3 on the ability of HCC cells to confer invasive and migratory properties. Huh7 cells with ANXA3 knockdown resulted in a significant decreased ability to invade and migrate, as evident by transwell migration and Matrigel invasion assays, respectively (FIG. 2G; * p-value<0.05).

Example 5

ANXA3 Confers Cancer and Stem Cell-Like Properties Via a Deregulated JNK Pathway in HCC In hope to delineate the mechanism by which ANXA3 mediates cancer and stem cell-like properties in HCC, the inventors employed gene expression profiling by cDNA microarray in two ANXA3 repressed cell lines (PLC8024 and Huh7). Pathway enrichment analysis on the commonly deregulated genes revealed an ANXA3-dependent signaling pathway network involving cell surface receptor linked signal transduction, intracellular signaling cascade, cell adhesion, and cell proliferation. Further analysis by pathway enrichment bioinformatics found ANAX3 to be associated with JNK/AP-1 signaling cascade, a pathway which has previously been shown to play a critical role in deregulated HCC. To study whether JNK pathway is involved in ANXA3-driven HCC, the expressions of JNK pathway-related proteins in ANXA3 knockdown cells were examined by Western Blotting. The inventors found that ANXA3 knockdown resulted in deregulation of the key players in the pathway including phospho-MKK4, phospho-JNK1, as well as its downstream targets c-myc and p21 (FIG. 2H). Similar results were also obtained in another HCC cell line model, PLC8024, for all the in vitro and in vivo assays tested above. Moreover, addition of JNK inhibitor SP600125 resulted in a decrease in ANXA3 expression concomitant with deregulated c-myc and p21, indicating that ANXA3 is a possible downstream target of JNK and the existence of a positive feedback loop. To further confirm the importance of JNK pathway in ANXA3-driven HCC, the inventors assessed the ability of JNK inhibitor in suppressing the cancer and stem cell-like properties driven by ANXA3 overexpression. Treatment of ANXA3 overexpressed cells with the JNK inhibitor SP600125 significantly reduced migration, invasion, angiogenesis, and resistance towards apoptosis induced by STS. Collectively, these data indicate that ANXA3 is functionally involved in driving HCC via a deregulated JNK pathway. ANXA3 knockdown resulted in a significant deregulation of key players in the pathway including p-MKK4, p-JNK1, c-myc and p21.

Example 6

Development of a Novel ANXA3 Neutralizing Monoclonal Antibody for the Therapeutic Targeting of HCC The inventors have now successfully developed a novel, custom-made ANXA3 monoclonal neutralizing antibody. Validation of the specificity of this antibody was evaluated by Western blot in a panel of liver cell lines (HepG2, MIHA, Hep3B, Huh7, PLC8024, SNU182, SNU475 and MHCC-97L). Western blot with the antibody revealed a very specific band at the predicted ANXA3 molecular weight (FIG. 3A). The effect of ANXA3 antibody in conferring cancer and stem cell-like features in HCC was subsequently investigated as further described below.

Example 7

Effect of ANXA3 Monoclonal Antibody on HCC Cell Proliferation In Vitro

The therapeutic role of ANXA3 to suppress cancer and stem cell-like properties in HCC was investigated in vitro using a newly developed monoclonal antibody against ANXA3 (SEQ ID NO: 1), developed in collaboration with Abmart, Shanghai.

The effect of ANXA3 monoclonal antibody on proliferation of HCC cells was investigated by XTT cell proliferation assay. Administration of 25 µg/ml of ANXA3 monoclonal antibody resulted in the inhibition of proliferation of HCC Huh7 and PLC8024 cells, but not in the immortalized normal MIHA cells (p-value<0.05). Control—isotype IgG monoclonal antibody administered at equal concentrations.

A total of 2000 single Huh7, PLC8024 HCC or immortalized normal MIHA liver cells were cultured in complete medium in 96-well plates, in the presence of a control IgG isotype monoclonal antibody or ANXA3 monoclonal antibody (25 µg/ml or 50 µg/ml), and allowed to grow for a total of 5 days. Proliferation rates were determined using XTT Cell proliferation assays (Roche Diagnostics) according to manufacturer's instructions. Absorbance was measured with a spectrophotometer (Tecan Sunrise) at 492 nm with a reference wavelength of 630 nm. XTT measurement was performed daily for a total of 5 days. ANXA3 antibody significantly reduced proliferation rate of HCC Huh7 and PLC8024 cells, but not the immortalized normal liver cell MIHA (FIG. 3B).

Example 8

Effect of ANXA3 Monoclonal Antibody on HCC Self-Renewal In Vitro

The effect of ANXA3 antibody on HCC self-renewal was investigated by spheroid formation assay in vitro (FIG. 3C). Administration of 25 µg/ml of ANXA3 monoclonal antibody resulted in the complete abolishment of spheroid formation in HCC Huh7 cells. Control—isotype IgG monoclonal antibody administered at the same concentration.

A total of 1000 single Huh7 HCC cells were cultured in the presence of a control IgG isotype monoclonal antibody (25 µg/ml) or anti-ANX3 monoclonal antibody (25 µg/ml) in 300 µl of serum-free DMEM/F12 medium (Invitrogen), supplemented with 4 µg/ml insulin (Sigma-Aldrich), B27 (1:50; Invitrogen), 20 ng/ml recombinant EGF (Sigma-Aldrich), 10 ng/ml recombinant basic FGF (Invitrogen), 500

U/ml penicillin (Invitrogen) and 500 µg/ml streptomycin (Invitrogen). Cells were cultured in suspension in poly-HEMA-coated 24-well plates. Cells were replenished with 30 µl of supplemented medium every second day. Spheroids were cultured for 14 days. ANXA3 antibody significantly reduced the number and size of spheroids (FIG. 3C).

Example 9

Effect of ANXA3 Monoclonal Antibody on Capillary Tube Formation in HUVEC Cells

The effect of ANXA3 antibody on HCC angiogenesis was investigated by capillary tube formation in vitro (FIG. 3C). Administration of 25 µg/ml of ANXA3 monoclonal antibody in the conditioned medium collected from Huh7 cells resulted in reduced capillary formation in HUVEC cells. Control—isotype IgG monoclonal antibody administered at the same concentration.

Huh7 cells incubated with control IgG isotype monoclonal antibody (25 µg/ml) or ANXA3 monoclonal antibody (25 µg/ml) were cultured in serum-free medium for 72 hrs. Conditioned media were collected and filtered for subsequent treatment of human umbilical vein endothelial cells (HUVECs) (Invitrogen). A total of $1 \times 10^4$ HUVECs were seeded into 96-well plate pre-coated with 50 µl Matrigel (BD Biosciences) and co-cultured with conditioned medium for 4 hrs. The formation of tube-like structures was examined and photographed using an inverted microscope. ANXA3 antibody significantly reduced the number of capillary tubes formed (FIG. 3C).

Example 10

Effect of ANXA3 Monoclonal Antibody on HCC Migration In Vitro

The effect of ANXA3 antibody on HCC migration was investigated by transwell migration in vitro (FIG. 3C). Administration of 25 µg/ml of ANXA3 monoclonal antibody resulted in reduced migration capacity of HCC Huh7 cells. Control—isotype IgG monoclonal antibody administered at the same concentration.

Migration assays were performed in 24-well millicell hanging inserts with polycarbonate membranes of 8.0 µm pore size (Millipore). In brief, $1 \times 10^5$ cells were added to the top chamber, and 10% FBS in DMEM was added to the bottom chamber as a chemoattractant. ANXA3 monoclonal antibody (25 µg/ml) was added into both the upper and lower chambers of the insert. After 48 hrs incubation at 37° C., migrated cells on the lower surface of the membrane were fixed with methanol and stained with crystal violet. The number of cells that invaded through the membrane was counted in 10 random fields under a 20× objective lens and imaged using imaging software. Anti-ANAX3 antibody significantly reduced the ability of HCC cells to migrate (FIG. 3C).

Treatment of HCC cells Huh7 with the ANXA3 neutralizing monoclonal antibody resulted in a deregulated expression of key players in the JNK pathway including p-JNK, c-myc and p21 (FIG. 3D).

Example 11

Effect of ANXA3 Knockdown and ANXA3 Antibody Treatment on JNK

To investigate whether the inhibition of tumor growth, self-renewal and metastasis by ANXA3 antibody treatment is related to the JNK pathway, Western blot analysis was performed on Huh7 and PLC8024 HCC cells with or without ANXA3 stably repressed or Huh7 cell lysates after treatment with ANXA3 antibody (FIG. 3D). NTC and mouse IgG isotype antibody was used for knockdown and neutralizing antibody treatment controls, respectively. Western blot was performed as described above with the following antibodies ANXA3 (Abcam), phosphorylated-MKK4 (Cell Signaling), phosphorylated-JNK1 (Cell Signaling), total JNK (Cell Signaling), c-myc (Invitrogen) and p21 (Cell Signaling). KinaseSTAR JNK activity assay (BioVision) was also performed to measure JNK-specific activity through determining the phosphorylation of c-Jun by Western blotting using a phospho-c-Jun specific antibody.

Example 12

Effect of ANXA3 Antibody Treatment on Invasion, Spheroid Formation in Patient Samples, Chemotherapy Resistance, and Apoptosis In Vitro The ANXA3 monoclonal antibody, administered at 25 µg/ml, suppressed invasion of Huh7 cells (FIG. 3E) and spheroid formation of HCC patient samples (FIG. 3F). The ANXA3 monoclonal antibody also sensitized cells towards cisplatin treatment (FIG. 3G) and induced apoptosis (FIG. 3H). The ANXA3 antibody significantly reduced the ability of HCC cells to invade, form spheroids, and resist chemotherapy and apoptosis.

Example 13

Determination of Therapeutic Potential of ANXA3 Antibody In Vivo

Immunodeficient NOD-SCID mice transplanted subcutaneously with HCC Huh7 cells or HCC primary cells were injected with PBS, mouse IgG control ANXA3 mAb, cisplatin or a combination of ANXA3 mAb and cisplatin over a period of 3 weeks (FIGS. 4A, B and C). Administration of ANXA3 mAb resulted in marked suppression of tumor growth and abolishment of the CD133+ liver CSC subset. Treatment with ANXA3 mAb in combination with cisplatin showed a synergistic tumor suppressive effect compared with treatments with just ANXA3 mAb or cisplatin alone. Although treatment with cisplatin resulted in a marked reduction in tumor volume, the CD133+ liver CSC subset was enriched in the residual tumor, and, as shown in FIG. 4D, serial transplantation of this residual tumor into secondary mouse recipients resulted in tumor formation and recurrence. Conversely, secondary transplantation of residual tumors from ANXA3 mAb or ANXA3 mAb and cisplatin combination treatment did not result in any tumor formation.

CONCLUSION

The inventors have validated ANXA3 as a tumor marker for HCC in a large set of patient samples and confirmed that endogenous ANXA3 protein levels are up-regulated in HCC. In addition, by functional in vitro and in vivo knockdown assays (with ANAX3 specific shRNA sequences complementary to the cDNA sequences of SEQ ID NO: 2 and NO: 3), the inventors also demonstrated that ANXA3 levels positively regulates cancer and stem cell-like properties in HCC, including its ability to initiate tumor formation; induce angiogenesis, self-renewal, migration, and invasion;

and confer resistance to apoptosis and chemotherapeutic drugs (5-fluorouracil and cisplatin). The inventors confirmed that the up-regulation of ANXA3 in HCC tumor tissues would also lead to an elevation of serum ANXA3 protein level in patients and hence act as a useful diagnostic marker for the disease. ANXA3 protein was secreted from HCC cells as shown by Western blotting of ANAX3 in conditioned medium collected from HCC cell lines. They found ANAX3 was detectable from the culture supernatant, indicating that ANXA3 is a secretory protein detectable in HCC patient sera. Subsequent studies found serum ANXA3 levels to be significantly up-regulated in HCC patients (n=60) compared with normal healthy individuals (n=32) (p-value≤0.05); and that among the HCC patients, higher serum ANXA3 levels were significantly correlated with advanced tumor stages (p-value≤0.01).

The high fatality-to-case ratio associated with HCC is partially a result of the lack of symptoms in early stages. Curative resection can only be the treatment of choice for 25% of HCC patients. Early detection of HCC is therefore the key to improving survival. Serum ANXA3 determination enhances early detection of HCC, allowing for better treatment options and survival outcome.

As mentioned above, down-regulation of ANXA3 using short hairpin ribonucleic acid (shRNA) approach can significantly reduce the ability of HCC cells to initiate tumor formation, induce angiogenesis, metastasize, and self-renew. It also sensitizes HCC cells to become more sensitive to chemotherapeutic drugs and apoptosis. The use of ANXA3 inhibitors antibody is a practical and feasible approach for targeted cancer therapy. ANXA3 antibody was generated against the ANXA3 specific peptide ENRWGTDEDK. This ANXA3 antibody elicited an inhibitory growth effect in HCC cells Huh7 and PLC8024, but not in the immortalized liver cell MIHA. Addition of ANXA3 antibody resulted in the effective neutralization of both endogenous and secretory ANXA3. It also significantly retarded the ability of Huh7 HCC cells to initiate spheroid formation, migrate, and induce capillary tube formation in HUVEC cells. The inventors have previously shown that ANXA3 stimulates the JNK signaling pathway. To investigate whether the inhibition of HCC formation and progression by ANXA3 treatment is related to the JNK pathway, Western blot analysis was performed on cultured cell lysate after treatment with ANXA3 antibody. Addition of the antibody significantly reduced phosphorylation of JNK1, c-myc; concomitant with an increase in p21 expression.

A list of references follows, which refer to citations in the text. They are incorporated by reference to the extent they are not inconsistent with the teachings herein.

The embodiments as disclosed and described in the application are intended to be illustrative and explanatory, and not limiting. Modifications and variations of the disclosed embodiments, for example, of the processes and apparatuses employed (or to be employed) as well as of the compositions and treatments used (or to be used), are possible; all such modifications and variations are intended to be within the scope of this application.

It should be understood that one skilled in the art can modify and verify the present invention in light of the disclosure of the various embodiments of this invention. Such equivalents are encompassed in the scope of the claims appended hereto.

REFERENCES

The following and all other references referred to herein are incorporated by reference:

1. Adams G P, Weiner L M. Monoclonal antibody therapy of cancer. Nat Biotechnol 2005; 23: 1147-1157.
2. Fernando N H, Hurwitz H I. Targeted therapy of colorectal cancer: clinical experience with bevacizumab. Oncologist 2004; 9: 11-18.
3. Gebo K A, Chander G, Jenckes M W, Ghanem K G, Herlong H F, Torbenson M S, El-Kamary S S, Bass E B. Screening tests for hepatocellular carcinoma in patients with chronic hepatitis C: a systematic review. Hepatology 2002; 36: S84-92.
4. Johnson P J. The role of serum alpha-fetoprotein estimation in the diagnosis and management of hepatocellular carcinoma. Clin Liver Dis 2001: 5: 145-159.
5. Kollermann J, Schlomm T, Bang H, Schwall G P, von Eichel-Streiber C, Simon R, Schostak M, Huland H, Berg W, Sauter G, Klocker H, Schrateenholz A. Expression and prognostic relevance of annexin A3 in prostate cancer. Eur Urol 2008; 54: 1314-1323.
6. Liu Y F, Xiao Z Q, Li M X, Li M Y, Zhang P F, Li C, Li F, Chen Y H, Yi H, Yao H X, Chen Z C. Quantitative proteome analysis reveals annexin A3 as a novel biomarker in lung adenocarcinoma. J Pathol 2009; 217: 54-64.
7. MacDonald D J, Kelly A M. The rapid quantitation of serum alpha-fetoprotein by two-site micro enzyme immunoassay. Clin Chim Acta 1978: 87: 367-372
8. Schostak M, Schwall G P, Poznanovic S, Groebe K, Muller M, Messinger D, Miller K, Krause H, Pelzer A, Horninger W, Klocker H, Hennenlotter J, Feyerabend S, Stenzl A, Schrattenholz A. Annexin A3 in urine: a highly specific noninvasive marker for prostate cancer early detection. J Urol 2009; 181: 343-353.
9. Shak S. Overview of the trastuzumab (Herceptin) anti-HER2 monoclonal antibody clinical program in HER2-overexpressing metastatic HCC. Herceptin Multinational Investigator Study Group. Semin Oncol 1999; 26: 71-77
10. Taketa K. Alpha-fetoprotein: reevaluation in hepatology. Hepatology 1990; 12: 1420-1432.
11. Thoenes L, Hoehn M, Kashirin R, Ogris M, Arnold G J, Wagner E, Guenther M. In vivo chemoresistance of prostate cancer in metronomic cyclophosphamide therapy. J Proteomics 2010; 73: 1342-1354.
12. Tong S W, Yang Y X, Hu H D, An X, Ye F, Hu P, Ren H, Li S L, Zhang D Z. Proteomic investigation of 5-fluorouracil resistance in a human hepatocellular carcinoma cell line. J Cell Biochem 2012; 113: 1671-1680.
13. Tsai S T, Tsou C C, Mao W Y, Chang W C, Han H Y, Hsu W L, Li C L, Shen C N, Chen C H. Label-free quantitative proteomics of CD133-positive liver cancer stem cells. Proteome Sci 2012; 10: 69.
14. Vanhoefer U, Tewes M, Rojo F, Dirsch O, Schleucher N, Rosen O, Tillner J, Kovar A, Braun A H, Trarbach T, Seeber S, Harstrick A, Baselga J. Phase I study of the humanized antiepidermal growth factor receptor monoclonal antibody EMD72000 in patients with advanced solid tumors that express the epidermal growth factor receptor. J Clin Oncol. 2004; 22: 175-184.
15. von Schilling C. Immunotherapy with anti-CD20 compounds. Semin Cancer Biol 2003; 13: 211-222.
16. Willems A, Gauger K, Henrichs C, Harbeck N. Antibody therapy for HCC. Anticancer Res 2005; 25: 1483-1489.
17. Wozny W, Schroer K, Schwall G P, Poznanovic S, Stegmann W, Dietz K, Rogatsch H, Schaefer G, Huebl H, Klocker H, Schrattenholz A, Cahill M A. Differential radioactive quantification of protein abundance ratios between benign and malignant prostate tissues: cancer association of annexin A3. Proteomics 2007; 7: 313-322.
18. Wu N, Liu S, Guo C, Hou Z, Sun M Z. The role of annexin A3 playing in cancers. Clin Transl Oncol 2013; 15: 106-110.
19. Yan X D, Pan L Y, Yuan Y, Lang J H, Mao N. Identification of platinum-resistance associated proteins through proteomic analysis of human ovarian cancer cells and their platinum-resistant sublines. J Proteome Res 2007; 6: 772-780.
20. Yan X, Yin J, Yao H, Mao N, Yang Y, Pan L. Increased expression of annexin A3 is a mechanism of platinum resistance in ovarian cancer. Cancer Res 2010; 70: 1616-1624.
21. Yin J, Yan X, Yao X, Zhang Y, Shan Y, Mao N, Yang Y, Pan L. Secretion of annexin A3 from ovarian cancer cells and its association with platinum resistance in ovarian cancer patients. J Cell Mol Med 2012; 16: 337-348.
22. Zeng C, Ke Z, Song Y, Yao Y, Hu X, Zhang M, Li H, Yin J. Annexin A3 is associated with a poor prognosis in HCC and participates in the modulation of apoptosis in vitro by affecting the Bcl-2/Bax balance. Exp Mol Pathol 2013; 95: 23-31.

What is claimed is:

1. A method for detecting the presence of ANXA3 in a subject, the method comprising:
   (a) obtaining a biological sample from the subject, wherein the sample is liver tissue, liver cells, liver interstitial fluid, serum, or plasma;
   (b) contacting the biological sample with an antibody that specifically binds to a peptide consisting of the sequence of SEQ ID NO: 1; and
   (c) detecting the complex comprising ANXA3 protein and the antibody.

2. The method of claim 1, the method further comprising detecting the presence of ANXA3 in a control sample.

3. The method of claim 1, wherein the biological sample comprises cells from hepatocellular carcinoma (HCC).

4. The method of claim 2, wherein the control sample is obtained from a healthy individual that does not have HCC or any other cancer or disease, from an immortalized normal liver cell line, or from an individual who was successfully treated for HCC and is free from HCC.

5. The method of claim 1, wherein the antibody is a monoclonal antibody.

6. The method of claim 1, wherein the biological sample is serum or plasma.

* * * * *

UNITED STATES PATENT AND TRADEMARK OFFICE
CERTIFICATE OF CORRECTION

PATENT NO. : 9,487,831 B2
APPLICATION NO. : 14/485206
DATED : November 8, 2016
INVENTOR(S) : Stephanie Kwai Yee Ma, Man Tong and Xin-Yuan Guan It is certified that error appears in the above-identified patent and that said Letters Patent is hereby corrected as shown below:

In the Specification

Column 5,
Lines 66-67, "5-fluoruracil." should read --5-fluorouracil.--.

Column 6,
Lines 55-56, "or deoxyribonucleic" should read --or "deoxyribonucleic--.

Column 20,
Lines 21-22, "Cytometry
    Cells were treated" should read --Cytometry
    Mouse Hybridoma cell line ANXA3-3M1-Hyb is deposited with American Type
Culture Collection (ATCC), P.O. Box 1549, Manassas, Va. 20108, as accession
number PTA-121826 under conditions that assure that access to the cultures will be
available during the pendency of this patent application to one determined by the
Commissioner of Patents and Trademarks to be entitled thereto under 37 CFR 1.14
and 35 U.S.C. 122. The deposit will be available as required by foreign patent laws
in countries wherein counterparts of the subject application, or its progeny, are filed.
However, it should be understood that the availability of a deposit does not constitute
a license to practice the subject invention in derogation of patent rights granted by
governmental action.
    Cells were treated--.

Columns 20-21,
Lines 62-11, "significant.
    Mouse Hybridoma cell line ANXA3-3M1-Hyb is deposited with American Type
Culture Collection (ATCC), P.O. Box 1549, Manassas, Va. 20108, as accession
number PTA-121826 under conditions that assure that access to the cultures will be Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office* available during the pendency of this patent application to one determined by the Commissioner of Patents and Trademarks to be entitled thereto under 37 CFR 1.14 and 35 U.S.C. 122. The deposit will be available as required by foreign patent laws in countries wherein counterparts of the subject application, or its progeny, are filed. However, it should be understood that the availability of a deposit does not constitute a license to practice the subject invention in derogation of patent rights granted by governmental action.
    Example 1" should read --significant.
    Example 1--.

Column 21,
Line 48, "1E)" should read --1E).--.

Column 28,
Line 30, "367-372" should read --367-372.--.
Line 40, "71-77" should read --71-77.--.

SEQUENCE LISTING

```
<160> NUMBER OF SEQ ID NOS: 7

<210> SEQ ID NO 1
<211> LENGTH: 10
<212> TYPE: PRT
<213> ORGANISM: Homo sapiens

<400> SEQUENCE: 1

Glu Asn Arg Trp Gly Thr Asp Glu Asp Lys
1               5                   10

<210> SEQ ID NO 2
<211> LENGTH: 58
<212> TYPE: DNA
<213> ORGANISM: Artificial
<220> FEATURE:
<223> OTHER INFORMATION: cDNA sequence corresponding to a portion of
      ANXA3 mRNA

<400> SEQUENCE: 2
ccggccagat cagaaattga cctttctcga gaaaggtcaa tttctgatct ggttttttg      58

<210> SEQ ID NO 3
<211> LENGTH: 58
<212> TYPE: DNA
<213> ORGANISM: Artificial
<220> FEATURE:
<223> OTHER INFORMATION: cDNA sequence corresponding to a portion of
      ANXA3 mRNA

<400> SEQUENCE: 3
ccgggtaaga gattatccag actttctcga gaaagtctgg ataatctctt actttttg      58

<210> SEQ ID NO 4
<211> LENGTH: 323
<212> TYPE: PRT
<213> ORGANISM: Homo sapiens

<400> SEQUENCE: 4

Met Ala Ser Ile Trp Val Gly His Arg Gly Thr Val Arg Asp Tyr Pro
1               5                   10                  15

Asp Phe Ser Pro Ser Val Asp Ala Glu Ala Ile Gln Lys Ala Ile Arg
                20                  25                  30

Gly Ile Arg Thr Asp Glu Lys Met Leu Ile Ser Ile Leu Thr Glu Arg
            35                  40                  45

Ser Asn Ala Gln Arg Gln Leu Ile Val Lys Glu Tyr Gln Ala Ala Tyr
        50                  55                  60

Gly Lys Glu Leu Lys Asp Asp Leu Lys Gly Asp Leu Ser Gly His Phe
65                  70                  75                  80
```

```
Glu His Leu Met Val Ala Leu Val Thr Pro Pro Ala Val Phe Asp Ala
             85                  90                  95

Lys Gln Leu Lys Lys Ser Met Lys Gly Ala Gly Thr Asn Glu Asp Ala
        100                 105                 110

Leu Ile Glu Ile Leu Thr Thr Arg Thr Ser Arg Gln Met Lys Asp Ile
            115                 120                 125

Ser Gln Ala Tyr Tyr Thr Val Tyr Lys Lys Ser Leu Gly Asp Asp Ile
        130                 135                 140

Ser Ser Glu Thr Ser Gly Asp Phe Arg Lys Ala Leu Leu Thr Leu Ala
145                 150                 155                 160

Asp Gly Arg Arg Asp Glu Ser Leu Lys Val Asp Glu His Leu Ala Lys
                165                 170                 175

Gln Asp Ala Gln Ile Leu Tyr Lys Ala Gly Glu Asn Arg Trp Gly Thr
            180                 185                 190

Asp Glu Asp Lys Phe Thr Glu Ile Leu Cys Leu Arg Ser Phe Pro Gln
        195                 200                 205

Leu Lys Leu Thr Phe Asp Glu Tyr Arg Asn Ile Ser Gln Lys Asp Ile
        210                 215                 220

Val Asp Ser Ile Lys Gly Glu Leu Ser Gly His Phe Glu Asp Leu Leu
225                 230                 235                 240

Leu Ala Ile Val Asn Cys Val Arg Asn Thr Pro Ala Phe Leu Ala Glu
                245                 250                 255

Arg Leu His Arg Ala Leu Lys Gly Ile Gly Thr Asp Glu Phe Thr Leu
            260                 265                 270

Asn Arg Ile Met Val Ser Arg Ser Glu Ile Asp Leu Leu Asp Ile Arg
        275                 280                 285

Thr Glu Phe Lys Lys His Tyr Gly Tyr Ser Leu Tyr Ser Ala Ile Lys
        290                 295                 300

Ser Asp Thr Ser Gly Asp Tyr Glu Ile Thr Leu Leu Lys Ile Cys Gly
305                 310                 315                 320

Gly Asp Asp

<210> SEQ ID NO 5
<211> LENGTH: 1634
<212> TYPE: DNA
<213> ORGANISM: Homo sapiens

<400> SEQUENCE: 5
gggtggggaa gcttagagac cggtgaggga gcagagctgg ggcgcctgtg tacagggata      60
gagcccggcg gcagcagggc gcggcttccc tttcccgggg cctggggccg caatcaggtg     120
gagtcgagag gccggaggag gggcaggagg aagggggtgcg gtcgcgatcc ggacccggag    180
ccagcgcgga gcacctgcgc ccgcggctga caccttcgct cgcagtttgt tcgcagttta    240
ctcgcacacc agtttccccc accgcgcttt ggattagtgt gatctcagct caaggcaaag    300
gtgggatatc atggcatcta tctgggttgg acaccgagga acagtaagag attatccaga    360
ctttagccca tcagtggatg ctgaagctat tcagaaagca atcagaggaa ttggaactga    420
tgagaaaatg ctcatcagca ttctgactga gaggtcaaat gcacagcggc agctgattgt    480
taaggaatat caagcagcat atggaaagga gctgaaagat gacttgaagg gtgatctctc    540
tggccacttt gagcatctca tggtggccct agtgactcca ccagcagtct ttgatgcaaa    600
gcagctaaag aaatccatga agggcgcggg aacaaacgaa gatgccttga ttgaaatctt    660
aactaccagg acaagcaggc aaatgaagga tatctctcaa gcctattata cagtatacaa    720
```

-continued

```
gaagagtctt ggagatgaca ttagttccga aacatctggt gacttccgga aagctctgtt      780
gactttggca gatggcagaa gagatgaaag tctgaaagtg gatgagcatc tggccaaaca      840
agatgcccag attctctata aagctggtga gaacagatgg ggcacggatg aagacaaatt      900
cactgagatc ctgtgtttaa ggagctttcc tcaattaaaa ctaacatttg atgaatacag      960
aaatatcagc caaaggaca ttgtggacag cataaaagga gaattatctg ggcattttga      1020
agacttactg ttggccatag ttaattgtgt gaggaacacg ccggccttt tagccgaaag      1080 actgcatcga gccttgaagg gtattggaac tgatgagttt actctgaacc gaataatggt      1140
gtccagatca gaaattgacc ttttggacat tcgaacagag ttcaagaagc attatggcta      1200
ttccctatat tcagcaatta aatcggatac ttctggagac tatgaaatca cactcttaaa      1260
aatctgtggt ggagatgact gaaccaagaa gataatctcc aaaggtccac gatgggcttt      1320
cccaacagct ccaccttact tcttctcata ctatttaaga gaacaagcaa atataaacag      1380
caacttgtgt tcctaacagg aattttcatt gttctataac aacaacaaca aaagcgatta      1440
ttattttaga gcatctcatt tataatgtag cagctcataa atgaaattga aaatggtatt      1500
aaagatctgc aactactatc caacttatat ttctgctttc aaagttaaga atctttatag      1560
ttctactcca ttaaatataa agcaagataa taaaaattgt tgcttttgtt aaaagtaaaa      1620
aaaaaaaaaa aaaa                                                         1634

<210> SEQ ID NO 6
<211> LENGTH: 20
<212> TYPE: DNA
<213> ORGANISM: Artificial
<220> FEATURE:
<223> OTHER INFORMATION: nucleotide primer sequence specific for ANXA3

<400> SEQUENCE: 6
gcaggaggaa ggggtgcggt                                                     20

<210> SEQ ID NO 7
<211> LENGTH: 20
<212> TYPE: DNA
<213> ORGANISM: Artificial
<220> FEATURE:
<223> OTHER INFORMATION: nucleotide primer sequence specific for ANXA3

<400> SEQUENCE: 7
tccaaagcgc ggtgggggaa                                                     20
```